US009068232B2

(12) United States Patent
Rosenfeld et al.

(10) Patent No.: US 9,068,232 B2
(45) Date of Patent: Jun. 30, 2015

(54) GENE EXPRESSION SIGNATURE FOR CLASSIFICATION OF KIDNEY TUMORS

(75) Inventors: Nitzan Rosenfeld, Cambridge (GB); Yael Spector, Tel Aviv (IL); Eddie Friedman, Kfar-Sava (IL); Zohar Dotan, Hod Hasharon (IL); Shai Rosenwald, Nes Ziona (IL)

(73) Assignees: Rosetta Genomics Ltd., Rehovot (IL); Tel Hashomer Medical Research Infrastructure and Services Ltd., Ramat Gan (IL)

( * ) Notice: Subject to any disclaimer, the term of this patent is extended or adjusted under 35 U.S.C. 154(b) by 56 days.

(21) Appl. No.: 13/412,020

(22) Filed: Mar. 5, 2012

(65) Prior Publication Data

US 2012/0157344 A1 Jun. 21, 2012

Related U.S. Application Data

(63) Continuation-in-part of application No. 13/057,750, filed as application No. PCT/IL2009/000765 on Aug. 5, 2009, now abandoned.

(60) Provisional application No. 61/086,483, filed on Aug. 6, 2008, provisional application No. 61/158,368, filed on Mar. 8, 2009, provisional application No. 61/453,142, filed on Mar. 16, 2011.

(51) Int. Cl.
*C12Q 1/68* (2006.01)
*G06F 19/24* (2011.01)
*G06F 19/20* (2011.01)

(52) U.S. Cl.
CPC ........ *C12Q 1/6886* (2013.01); *C12Q 2600/112* (2013.01); *C12Q 2600/158* (2013.01); *C12Q 2600/178* (2013.01); *G06F 19/20* (2013.01); *G06F 19/24* (2013.01)

(58) Field of Classification Search
None
See application file for complete search history.

(56) References Cited

U.S. PATENT DOCUMENTS

| 8,288,356 B2 * | 10/2012 | Obad et al. ............ 514/44 A |
|---|---|---|
| 2005/0107325 A1 | 5/2005 | Manoharan |
| 2005/0182005 A1 | 8/2005 | Tuschl |
| 2006/0292617 A1 | 12/2006 | Neely et al. |
| 2007/0065844 A1 | 3/2007 | Golub et al. |
| 2007/0092882 A1 | 4/2007 | Wang et al. |
| 2008/0182239 A1 | 7/2008 | Mullinax et al. |

FOREIGN PATENT DOCUMENTS

| WO | WO-2004/032842 A2 | 4/2004 |
|---|---|---|
| WO | WO 2007148235 A2 * | 12/2007 |
| WO | WO 2011024157 A1 * | 3/2011 |

OTHER PUBLICATIONS

Singer et al. Targeted therapies for non-clear renal cell carcinoma. Targeted Oncology, vol. 5, No. 2, pp. 119-129, Jun. 2010.*
Tazi et al. Advanced treatments in non-clear renal cell carcinoma. Urology Journal, vol. 8, No. 1, pp. 1-11, Winter 2011.*
Spector et al. Development and validation of a microRNA-based diagnostic assay for classification of renal cell carcinomas. Molecular Oncology, vol. 7, pp. 732-738, Mar. 2013.*
Wu, B. Differential gene expression detection and sample classification using penalized linear regression models. Bioinformatics, vol. 22, No. 4, pp. 472-476, 2006.*
Jing et al. Comparison of supervised clustering methods for the analysis of DNA microarray expression data. Agricultural Sciences in China, vol. 7, No. 2, pp. 129-139, Feb. 2008.*
Allory et al., "Profiling and classification tree applied to renal epithelial tumours," Histopathology, 2008, pp. 158-166, vol. 52.
Bartel et al., "MicroRNAs: At the Root of Plant Development?," Plant Physiology, Jun. 2003, pp. 709-717, vol. 132.
Bartel, D.P., "MicroRNAs: Genomics, Biogenesis, Mechanism, and Function," Cell, Jan. 2004, pp. 281-297, vol. 116.
Brennecke et al., "Principles of MicroRNA-Target Recognition," PLoS Biology, Mar. 2005, pp. 404-418, vol. 3, No. 3, e85.
Jemal et al., "Cancer Statistics, 2008," CA Cancer J Clin, Mar./Apr. 2008, pp. 71-96, vol. 58, No. 2.
Krek et al., "Combinatorial microRNA target predictions," Nature Genetics, May 2005, pp. 495-500, vol. 37, No. 5.
Krützfeldt et al., "Silencing of microRNAs in vivo with 'antagomirs,'" Nature, 2005, pp. 1-5.
Lewis et al., "Conserved Seed Pairing, Often Flanked by Adenosines, Indicates that Thousands of Human Genes are MicroRNA Targets," Cell, Jan. 2005, pp. 15-20, vol. 120.
Lopez-Beltran et al., "Targeted therapies and biological modifiers in urologic tumors: pathobiology and clinical implications," Seminars in Diagnostic Pathology, Nov. 2008, pp. 232-244, vol. 25, No. 4.
Ma et al., "Molecular Classification of Human Cancers Using a 92-Gene Real-Time Quantitative Polymerase Chain Reaction Assay," Arch Pathol Lab Med, Apr. 2006, pp. 465-473, vol. 130.
Shannon et al., "The Value of Preoperative Needle Core Biopsy for Diagnosing Benign Lesions Among Small, Incidentally Detected Renal Masses," J Urology, Oct. 2008, pp. 1257-1261, vol. 180.
Soutschek et al., "Therapeutic silencing of an endogenous gene by systemic administration of modified siRNAs," Nature, Nov. 2004, pp. 173-178, vol. 432.
Yekta et al., "MicroRNA-Directed Cleavage of *HOXB8* mRNA," Science, Apr. 2004, pp. 594-596, vol. 304.
Akobeng, AK. Understanding diagnostic tests 3: receiver operating characteristic curves. Acta Paediatrica, vol. 96, pp. 644-647,2007.
Chen et al. Messenger RNA expression ratios among four genes predict subtypes of renal cell carcinoma and distinguish oncocytoma from carcinoma. Clinical Cancer Research, vol. 11, No. 18, pp. 6558-6566, Sep. 2005.

(Continued)

*Primary Examiner* — Jennifer Dunston
(74) *Attorney, Agent, or Firm* — Ron Galant; Polsinelli PC

(57) ABSTRACT

The present invention provides a method for classification of kidney tumors through the analysis of the expression patterns of specific microRNAs and nucleic acid molecules relating thereto. Classification according to a microRNA expression framework allows optimization of treatment, and determination of specific therapy.

8 Claims, 12 Drawing Sheets

(56) References Cited

OTHER PUBLICATIONS

Chen et al. Real-time quantification of microRNAs by stem-loop RT-PCR. Nucleic Acids Research, vol. 33, No. 20, p. e179, Nov. 2005, printed as pp. 1/9 to 9/9.

Golub et al. Molecular classification of cancer: Class discovery and class prediction by gene expression monitoring. Science, vol. 286, pp. 531-537, Oct. 1999.

Landgraf et al. A mammalian microRNA expression atlas based on small RNA library sequencing. Cell, vol. 129, pp. 1401-1414, Jun. 29, 2007, including the entry for hsa-miR-455 of Table S12.

Liu et al. Patterns of known and novel small RNAs in human cervical cancer. Cancer Research, vol. 67, pp. 6031-6043, Jul. 6, 2007.

miRNA entry for M10003513, printed from http://www/mirbase.org/cgi-bin/mirna_entry.pl?acc=MIOOO3513 as pp. 1/4 to 4/4 on Dec. 20, 2012.

Pusztai and Hess. Clinical trial design for microarray predictive marker discovery and assessment. Annals of Oncology, vol. 15, pp. 1731-1737, 2004.

Shi et al. Facile means for quantifying microRNA expression by real-time PCR. BioTechniques, vol. 39, No. 4, pp. 519-524, Oct. 2005.

Office Action received in the related U.S. Appl. No. 13/057,750, dated Jan. 4, 2013.

Calin et al., "MicroRNA profiling reveals distinct signatures in B cell chronic lymphocytic leukemias," Proceedings of the National Academy of Sciences of USA, Aug. 2004, pp. 11755-11760, vol. 101.

Gottardo et al. Micro-RNA profiling in kidney and bladder cancers, Urologic Oncology, Sep. 2007, pp. 387-392, vol. 25, No. 5.

Higgins et al., "Gene expression patterns in renal cell carcinoma assessed by complementary DNA microarray," American Journal of Pathology, Mar. 2003. pp. 925-932, vol. 162, No. 3.

Hillig et al., "Identification of a miRNA Signature in Renal Cell Cancer," Journal of Urology, May 2008, p. 92, vol. 179, No. 4.

International Search Report mailed Dec. 3, 2009 in PCT/IL2009/000765.

Juan et al., "MicroRNA Expression Profile in Clear-Cell Kidney Cancer," Journal of Urology, May 2008, p. 92, vol. 179, No. 4.

Lu et al., MicroRNA expression profiles classify human cancers, Nature, Jun. 2005, pp. 834-838, vol. 435, No. 7043.

Rosenfeld et al., "MircoRNAs accurately identify cancer tissue origin," Nature Biotechnology, Apr. 2008, pp. 462-469, vol. 26, No. 4.

Sun et al., "Development of a micro-array to detect human and mouse microRNAs and characterization of expression in human organs," Nucleic Acids Research, 2004, p. E188, vol. 32, No. 22.

\* cited by examiner

GENE EXPRESSION SIGNATURE FOR CLASSIFICATION OF KIDNEY TUMORS

This application is a Continuation in Part of U.S. patent application Ser. No. 13/057,750, filed Feb. 4, 2011, now abandoned, which is a national stage entry of PCT/IL2009/000765, filed Aug. 5, 2009, which claims priority to U.S. Provisional Patent Application Nos. 61/086,423, filed Aug. 6, 2008, and 61/158,368, filed Mar. 8, 2009; this application claims the benefit of U.S. Provisional Patent Application No. 61/453,142, filed Mar. 16, 2011, all of which are incorporated herein by reference.

FIELD OF THE INVENTION

The present invention relates to methods for classification of kidney tumors. Specifically the invention relates to microRNA molecules associated with specific kidney tumors, as well as various nucleic acid molecules relating thereto or derived therefrom.

BACKGROUND OF THE INVENTION

In recent years, microRNAs (miRs) have emerged as an important novel class of regulatory RNA, which have a profound impact on a wide array of biological processes. These small (typically 18-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. The remarkable tissue-specificity of miR expression allows the development of novel approaches to molecular classification. There are currently about 1,100 known human miRs.

Renal cancers account for more than 3% of adult malignancies and cause more than 13,000 deaths per year in the US alone (Jemal, A., et al. 2008, Cancer statistics, CA Cancer J Clin 58, 71-96). The incidence of renal cancers in the US rose more than 50% between 1983 to 2002 and the estimated number of new cases per year rose from 39,000 estimated in 2006 to 54,000 estimated in 2008. Despite the trend of increased incidence of relatively small and kidney-confined disease, the rate of mortality has not changed significantly during the last 2 decades in the U.S. and Europe. In the 1980s, renal tumors were basically regarded as one disease: the higher the stage and the grade, the worse is the prognosis. After the 1980s, molecular biologists and pathologists described new entities with different morphological and biological characteristics. Evidence for different long-term prognosis for these subtypes makes the correct pathological diagnosis of a renal cancer critically important for the clinician. Currently, it is well accepted that renal cell carcinoma (RCC) is a family of carcinomas which arise from the epithelium of the renal tubules. The current classification of renal cell carcinoma includes four main types: Clear cell papillary, chromophobe, and collecting duct carcinoma, as well as unclassified renal cell carcinoma. Oncocytoma is a benign subtype of RCC.

Clear cell (conventional) renal carcinoma is the most frequent subtype of RCC and accounts for 60-70% of cases and account for the majority of renal cell cancer specific mortality. The term "conventional cell" is increasingly used to replace the name "clear cell", because some types have eosinophilic cytoplasm, generating a more difficult diagnostic challenge. In tumors of clear cell, a characteristic vascular network is commonly observed. The clear cell (conventional) cell carcinoma type is associated with germ line and somatic mutations of the von Hippel-Lindau (VHL) suppressor gene and such mutations might impact the prognosis and might predict response to drugs targeting the VHL pathway. Papillary RCC typically consists of a central fibrovascular core with epithelial covered papillae. It is subclassified into type 1 and 2 tumors that differ in terms of morphology, genotype and clinical outcome. Genetically, this type of tumor is associated with polysomies of chromosomes 7 or 17 and deficiency of Y. Chromophobe RCC was first described in the mid 80ies and prior to that would have likely been classified as clear cell (conventional) RCC or as (benign) oncocytoma. The typical form exhibits balloon cells with an abundant granular pale cytoplasm, or eosinophilic cytoplasm that resemble the cells of oncocytoma. Such features as described above are characteristic of the histological subtypes, but inter-observer variations limit the accuracy of histological classification, with some types identified with a sensitivity of 70% or lower. Furthermore, underlying biological mechanisms playing important roles in these tumors are yet to be elucidated.

These different histological subtypes of RCC vary in their clinical courses and their prognosis, and different clinical strategies have been developed for their management. Patients with conventional cell renal carcinoma have a poorer prognosis, and differences may also exist between the prognosis of patients with papillary or chromophobe RCC. The histological types arise through different constellations of genetic alterations, and show expression or mutation in different oncogenic pathways; they therefore offer different molecular candidates for targeted therapy (e.g., mTOR, VEGF, KIT). Initial studies show differences in the responses of RCC subtypes to targeted therapies (Lopez-Beltran, A., et al. 2008, Semin Diagn Pathol 25, 232-44), and future therapies are likely to be individualized for the different types. The correct identification of these subtypes is therefore important choice of treatment, and for the selection of patients for clinical trials.

Based on the growing clinical demand for accurate diagnosis of RCC subtypes, recent studies focused on the immunohistochemical profiling of different carcinomas. Allory et al lately described a subset of 12 antibodies as base for classification of renal cell carcinomas. In this report AMACR, CK7 and CD10 had the most powerful classification trees with 78%-87% of carcinomas correctly classified (Allory, Y., et al. 2008, Histopathology 52, 158-66). Immunohistochemistry provides limited information for distinguishing chromophobe RCC from oncocytoma. However, the increasing number of smaller tumors and needle-biopsy procedures places a strain on immunohistochemical methods. In a recent large study of 235 cases, more than 20% of the core needle biopsies were nondiagnostic (Shannon, B. A., et al. 2008, J Urol 180, 1257-61). This emphasized the need for developing additional types of molecular markers for the classification of renal tumors and for their study.

SUMMARY OF THE INVENTION

The present invention provides nucleic acid sequences for use in the identification, classification and diagnosis of particular subtypes of kidney tumors. The nucleic acid sequences can also be used as prognostic markers for prognostic evaluation and determination of appropriate treatment of a subject based on the abundance of the nucleic acid sequences in a biological sample.

The present invention further provides a method of classifying kidney tumors, the method comprising: obtaining a biological sample from a subject; determining expression of individual nucleic acids in a predetermined set of microRNAs; and classifying the specific subtype of kidney tumor in said sample.

The present invention is based in part on using microRNA microarrays with a training set of 181 formalin-fixed, paraffin-embedded (FFPE) renal tumor samples, and identifying microRNAs that have specific expression levels in distinct tumor types. Clustering showed a stronger similarity between oncocytoma and chromophobe subtypes, and between papillary and clear-cell tumors. By basing a classification algorithm on this structure, inherent biological correlations were followed, and could achieve accurate classification using few microRNAs markers.

According to one aspect, the present invention provides a method for the detection of a specific subtype of kidney tumor, the method comprising: obtaining a biological sample from a subject; determining an expression profile in said sample of nucleic acid sequences selected from the group consisting of SEQ ID NOS: 1-24, and a sequence having at least about 80% identity thereto; and comparing said expression profile to a reference value by using a classifier algorithm; whereby an altered expression levels of the nucleic acid sequence allows the detection of the specific subtype of kidney tumor in said sample.

According to certain embodiments, said specific subtype is selected from the group consisting of oncocytoma, clear cell RCC, papillary RCC and chromophobe RCC.

According to some embodiments, the classifier algorithm is selected from the group consisting of decision tree classifier, K-nearest neighbor classifier (KNN), logistic regression classifier, nearest neighbor classifier, neural network classifier, Gaussian mixture model (GMM), Support Vector Machine (SVM) classifier, nearest centroid or prototype classifier, linear regression classifier, random forest classifier and any other such classifier.

The invention further provides a method for distinguishing between chromophobe RCC and oncocytoma, the method comprising: obtaining a biological sample from a subject; determining in said sample an expression profile of nucleic acid sequences selected from the group consisting of SEQ ID NOS: 1-24 and a sequence having at least 80% identity thereto; and comparing said expression profile to a reference value; whereby a relative abundance of said nucleic acid sequences allows the detection of said oncocytoma or chromophobe RCC.

According to some embodiments, a relative abundance of nucleic acid sequences selected from the group consisting of SEQ ID NOS: 3, 5, 7, 9, 11, 12, 16, 18, 19, 23, and a sequence having at least 80% identity thereto is indicative of the presence of oncocytoma.

According to other embodiments, a relative abundance of nucleic acid sequences selected from the group consisting of SEQ ID NOS: 1, 2, 4, 6, 8, 10, 13-15, 17, 20-22, 24, and a sequence having at least 80% identity thereto is indicative of the presence of chromophobe RCC.

The invention further provides a method for distinguishing between clear cell RCC and papillary RCC, the method comprising: obtaining a biological sample from a subject; determining in said sample an expression profile of nucleic acid sequences selected from the group consisting of SEQ ID NOS: 1-24 and a sequence having at least 80% identity thereto; and comparing said expression profile to a reference value; whereby a relative abundance of said nucleic acid sequences allows the detection of said RCC.

According to some embodiments, a relative abundance of nucleic acid sequences selected from the group consisting of SEQ ID NOS: 3, 5-7, 9, 12, 24, and a sequence having at least 80% identity thereto is indicative of the presence of clear cell RCC.

According to other embodiments, a relative abundance of nucleic acid sequences selected from the group consisting of SEQ ID NOS: 1, 2, 4, 8, 10, 11, 13-23, and a sequence having at least 80% identity thereto is indicative of the presence of papillary RCC.

The invention further provides a method for distinguishing between chromophobe RCC, clear cell RCC, papillary RCC and oncocytoma, the method comprising: obtaining a biological sample from a subject; determining in said sample an expression profile of nucleic acid sequences selected from the group consisting of SEQ ID NOS: 1-24, and a sequence having at least 80% identity thereto; and comparing said expression profile to a reference value; whereby a relative abundance of said nucleic acid sequences allows the detection of said RCC.

In certain embodiments, the subject is a human.

In certain embodiments, the method is used to determine a course of treatment of the subject.

According to other embodiments, said biological sample is selected from the group consisting of bodily fluid, a cell line and a tissue sample. According to some embodiments, said tissue is a fresh, frozen, fixed, wax-embedded or formalin fixed paraffin-embedded (FFPE) tissue.

According to some embodiments said tissue sample is a kidney tumor sample.

According to some embodiments said tissue sample is selected from the group consisting of benign renal tissue sample and malignant renal tissue sample.

According to some embodiments, the method comprises determining the expression levels of at least one nucleic acid sequence. According to some embodiments the method further comprising combining one or more expression ratios. According to some embodiments, the expression levels are determined by a method selected from the group consisting of nucleic acid hybridization, nucleic acid amplification, and a combination thereof. According to some embodiments, the nucleic acid hybridization is performed using a solid-phase nucleic acid biochip array. According to certain embodiments, the nucleic acid hybridization is performed using in situ hybridization. According to some embodiments, the solid-phase nucleic acid biochip array method comprises hybridization with a probe. According to other embodiments, the probe comprises a nucleic acid sequence that is complementary to a sequence selected from the group consisting of SEQ ID NOS: 1-24, a fragment thereof and sequences at least about 80% identical thereto.

According to other embodiments, the nucleic acid amplification method is real-time PCR (RT-PCR). According to one embodiment, said real-time PCR is quantitative real-time PCR (qRT-PCR).

According to some embodiments, the RT-PCR method comprises forward and reverse primers. According to other embodiments, the forward primer comprises a sequence selected from the group consisting of SEQ ID NOS: 52-66, a fragment thereof and a sequence having at least about 80% identity thereto. According to other embodiments, the reverse primer comprises SEQ ID NO: 82, a fragment thereof and a sequence having at least about 80% identity thereto.

According to some embodiments, the real-time PCR method further comprises hybridization with a probe. According to other embodiments, the probe comprises a nucleic acid sequence that is complementary to a sequence selected from the group consisting of SEQ ID NOS: 1-24, a fragment thereof and sequences at least about 80% identical thereto.

According to other embodiments, the probe comprises a sequence selected from the group consisting of any one of SEQ ID NOS: 67-81, a fragment thereof and sequences at least about 80% identical thereto.

The invention further provides a kit for renal tumor classification; said kit comprises a probe comprising a nucleic acid sequence that is complementary to a sequence selected from the group consisting of SEQ ID NOS: 1-24, a fragment thereof and sequences having at least about 80% identity thereto.

According to some embodiments, said probe comprising a nucleic acid sequence selected from the group consisting of SEQ ID NOS: 67-81, a fragment thereof and a sequence at least about 80% identical thereto.

According to some embodiments, the kit further comprises forward and reverse primers. According to some embodiments, the forward primer comprising a sequence selected from the group consisting of SEQ ID NOS: 52-66, a fragment thereof and a sequence having at least about 80% identity thereto.

According to other embodiments, the reverse primer comprises SEQ ID NO: 82, a fragment thereof and sequences having at least about 80% identity thereto.

These and other embodiments of the present invention will become apparent in conjunction with the figures, description and claims that follow.

DETAILED DESCRIPTION OF THE INVENTION

Figure 1:
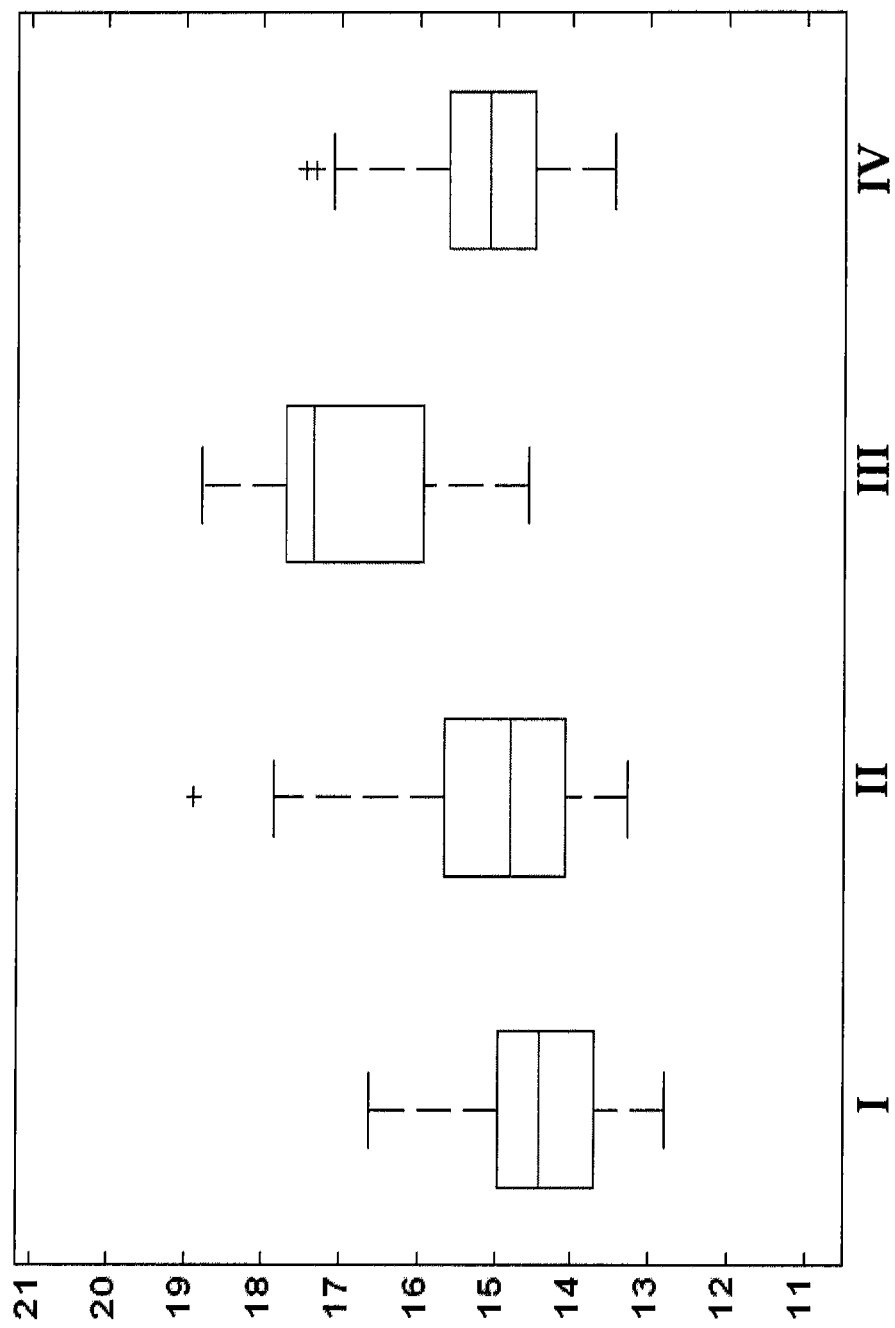
FIG. 1 shows boxplot indicating expression levels of MID-16582 (SEQ ID NO: 18) in normalized fluorescence units, as measured by a microarray in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 2:
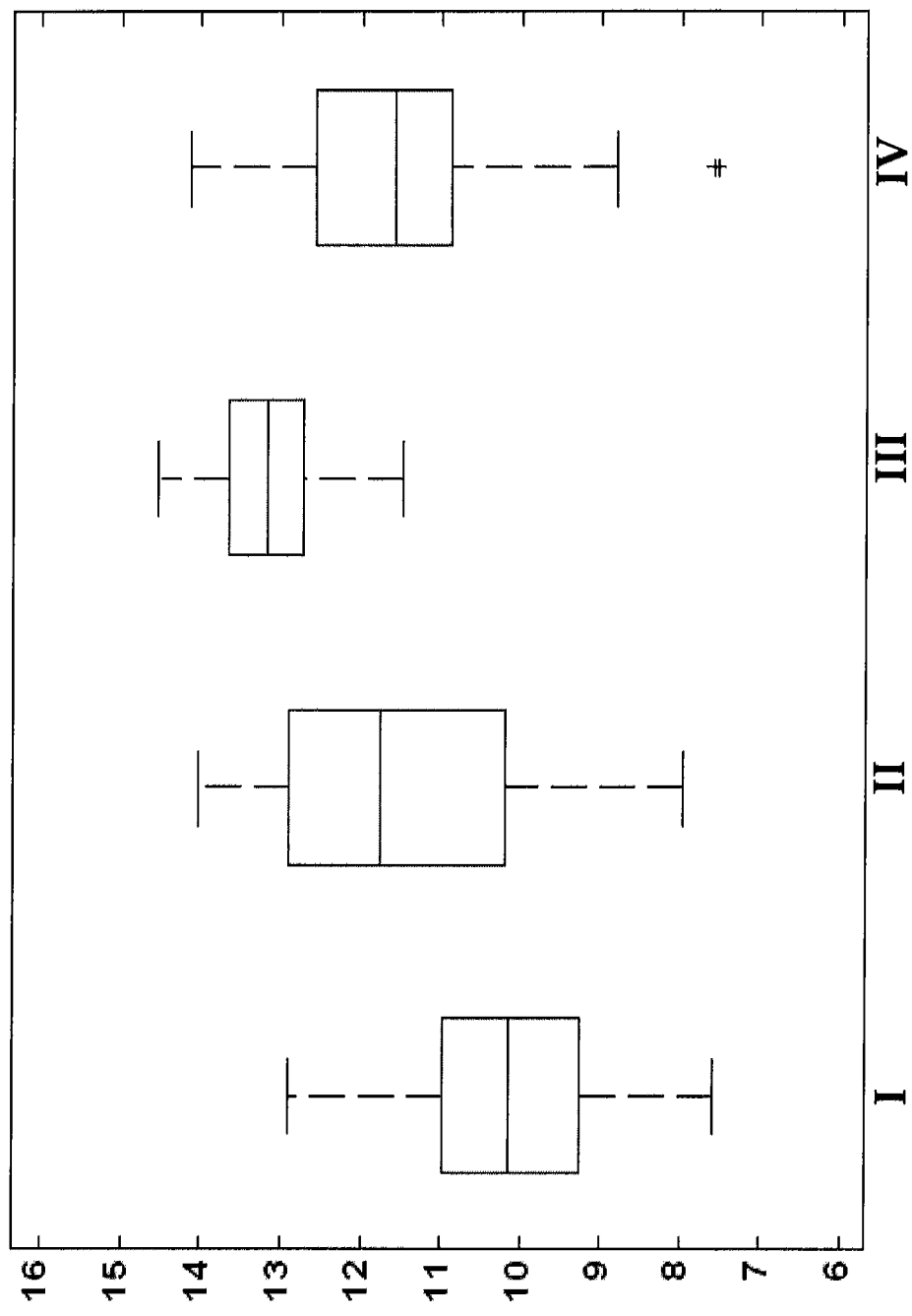
FIG. 2 shows boxplot indicating expression levels of MID-19962 (SEQ ID NO: 11) in normalized fluorescence units, as measured by a microarray in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 3:
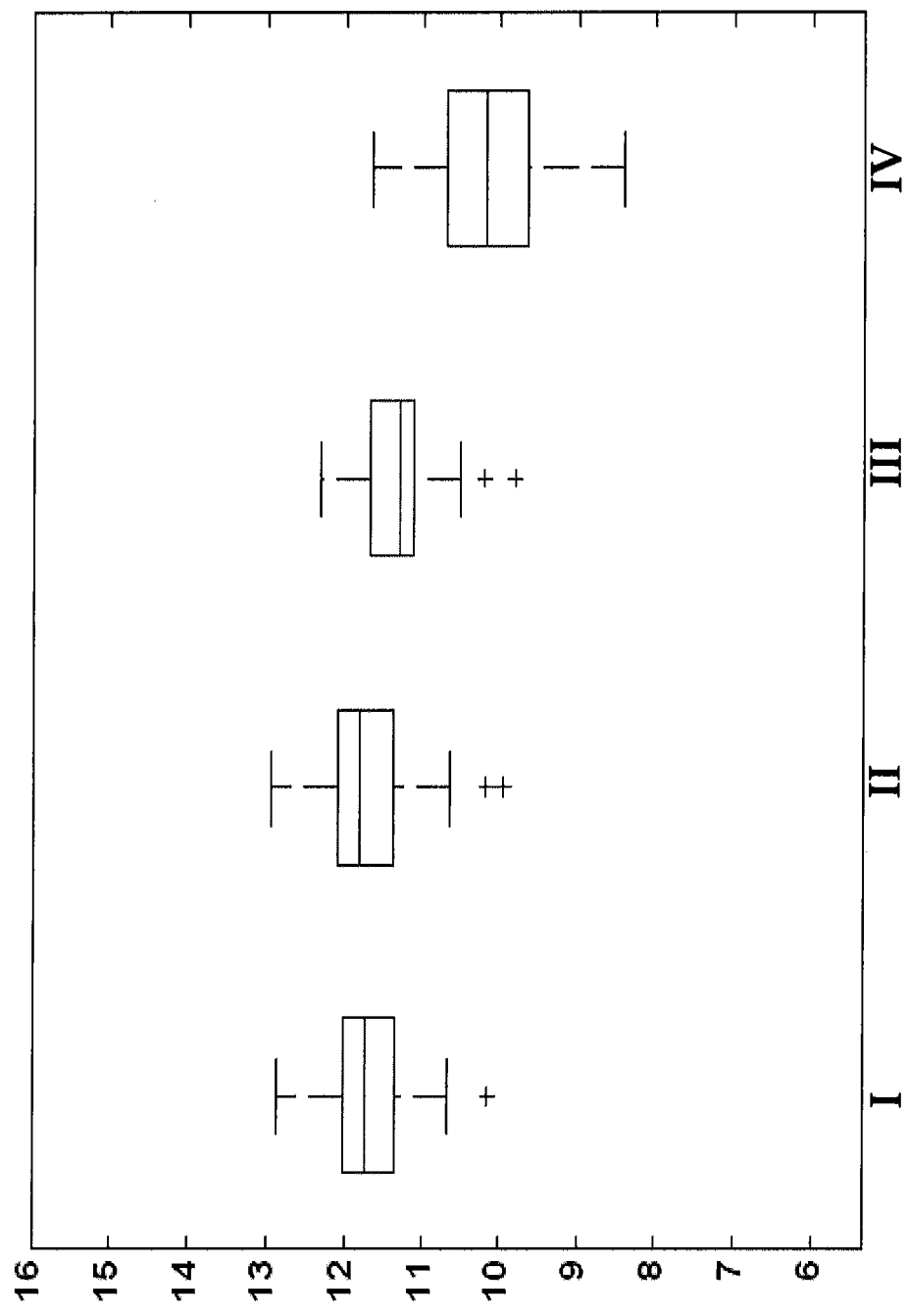
FIG. 3 shows boxplot indicating expression levels of miR-130a (SEQ ID NO: 19) in normalized fluorescence units, as measured by a microarray in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 4:
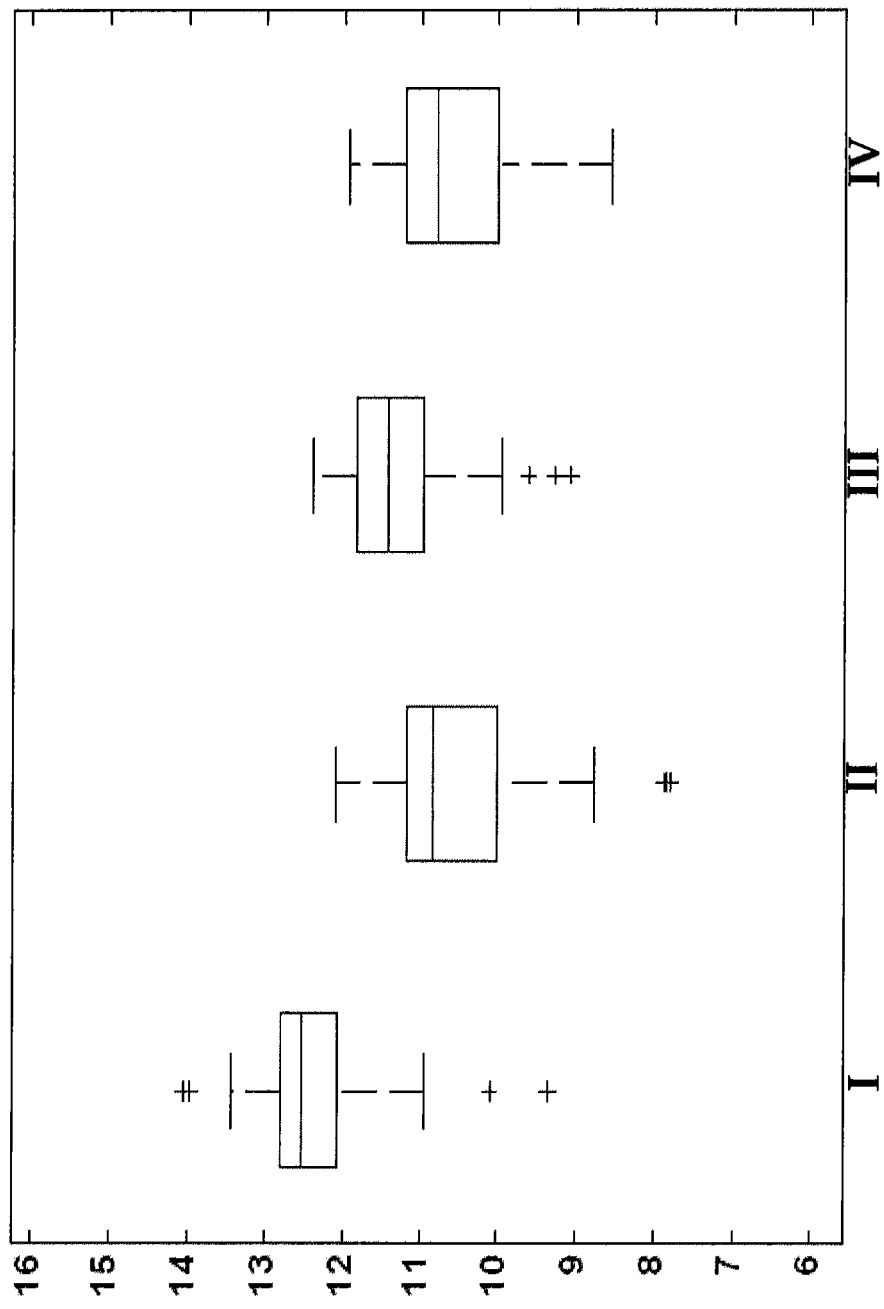
FIG. 4 shows boxplot indicating expression levels of miR-195 (SEQ ID NO: 9) in normalized fluorescence units, as measured by a microarray in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 5:
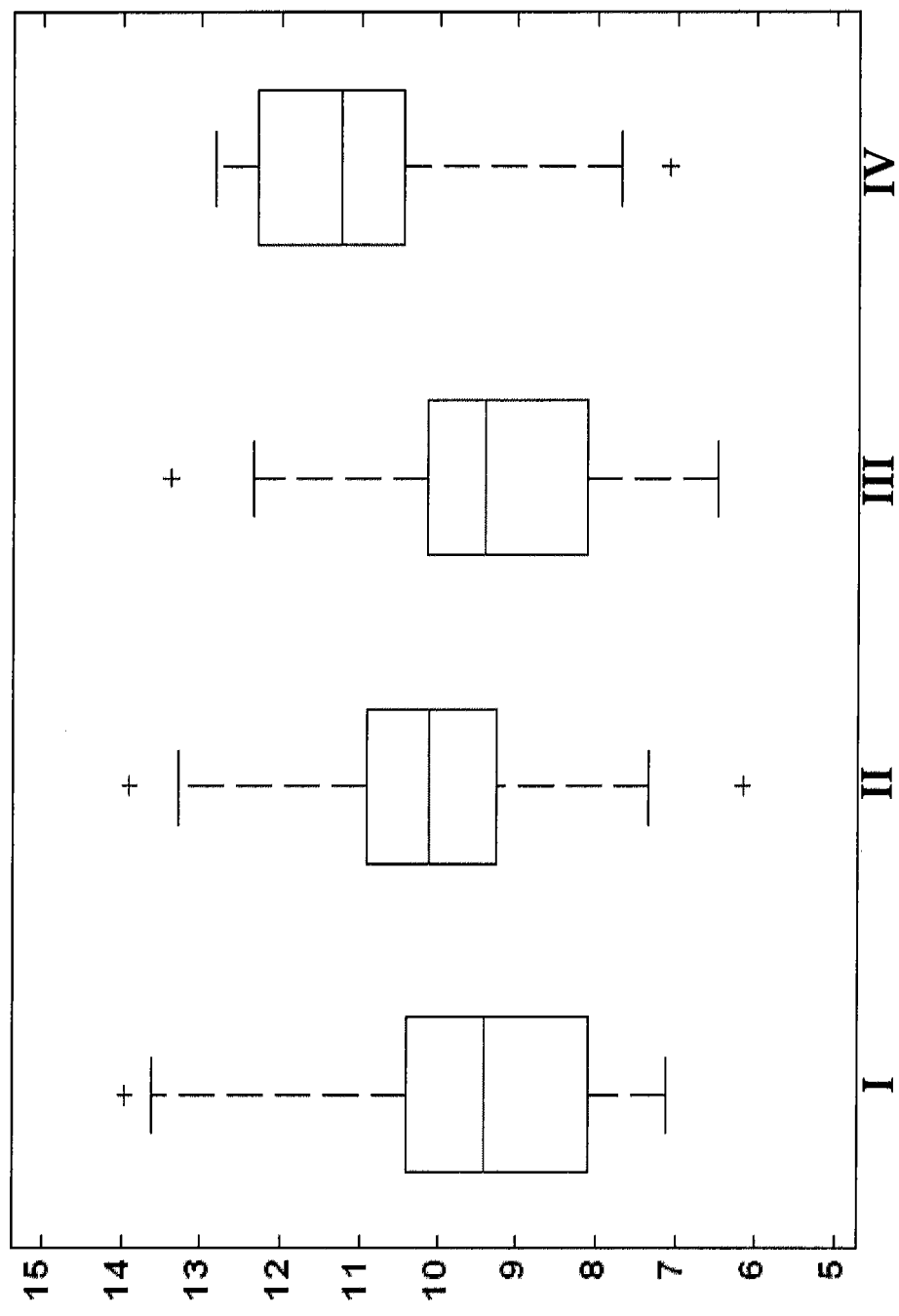
FIG. 5 shows boxplot indicating expression levels of MID-16869 (SEQ ID NO: 21) in normalized fluorescence units, as measured by a microarray in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 6:
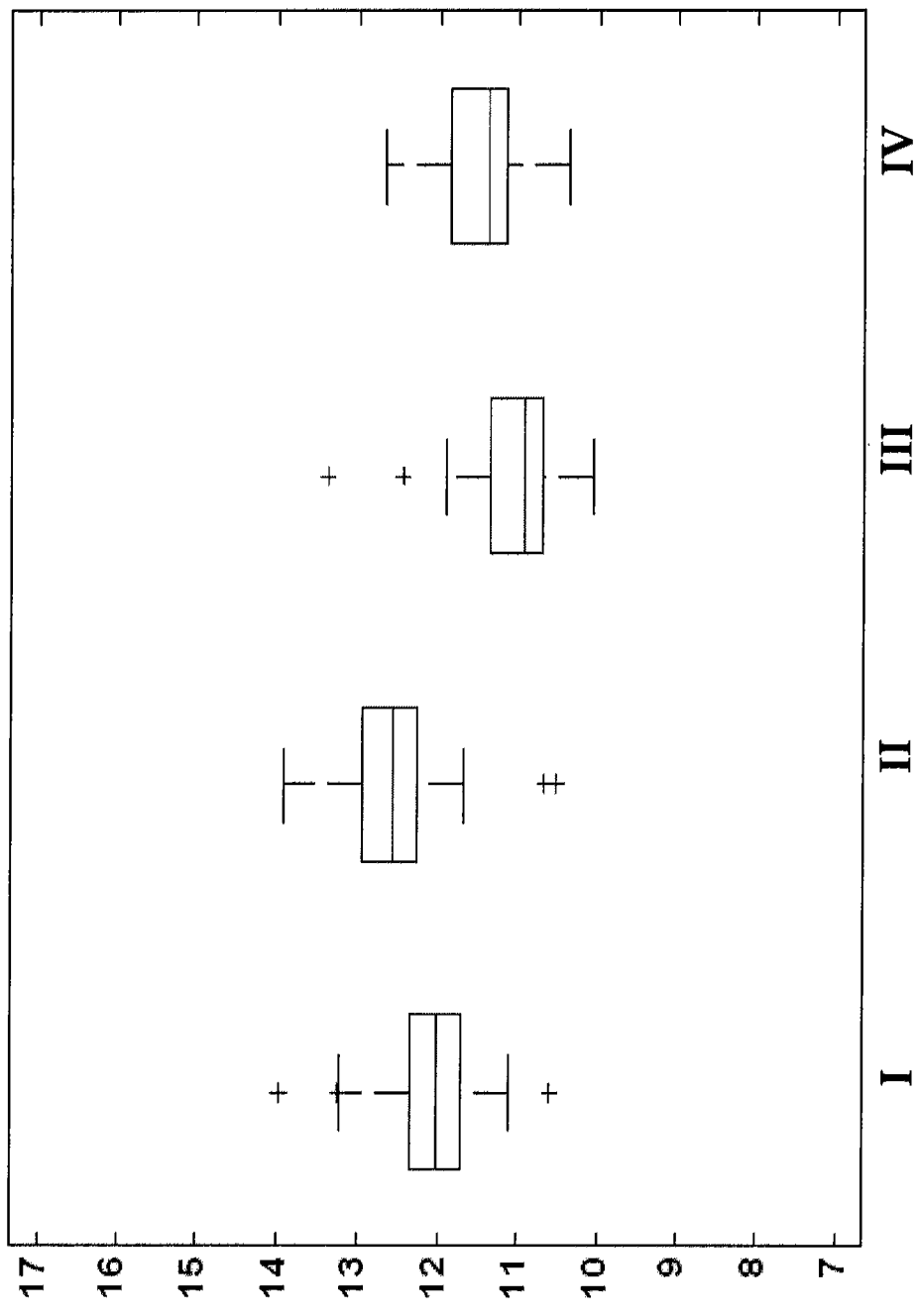
FIG. 6 shows boxplot indicating expression levels of miR-93(SEQ ID NO: 20) in normalized fluorescence units, as measured by a microarray in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 7:
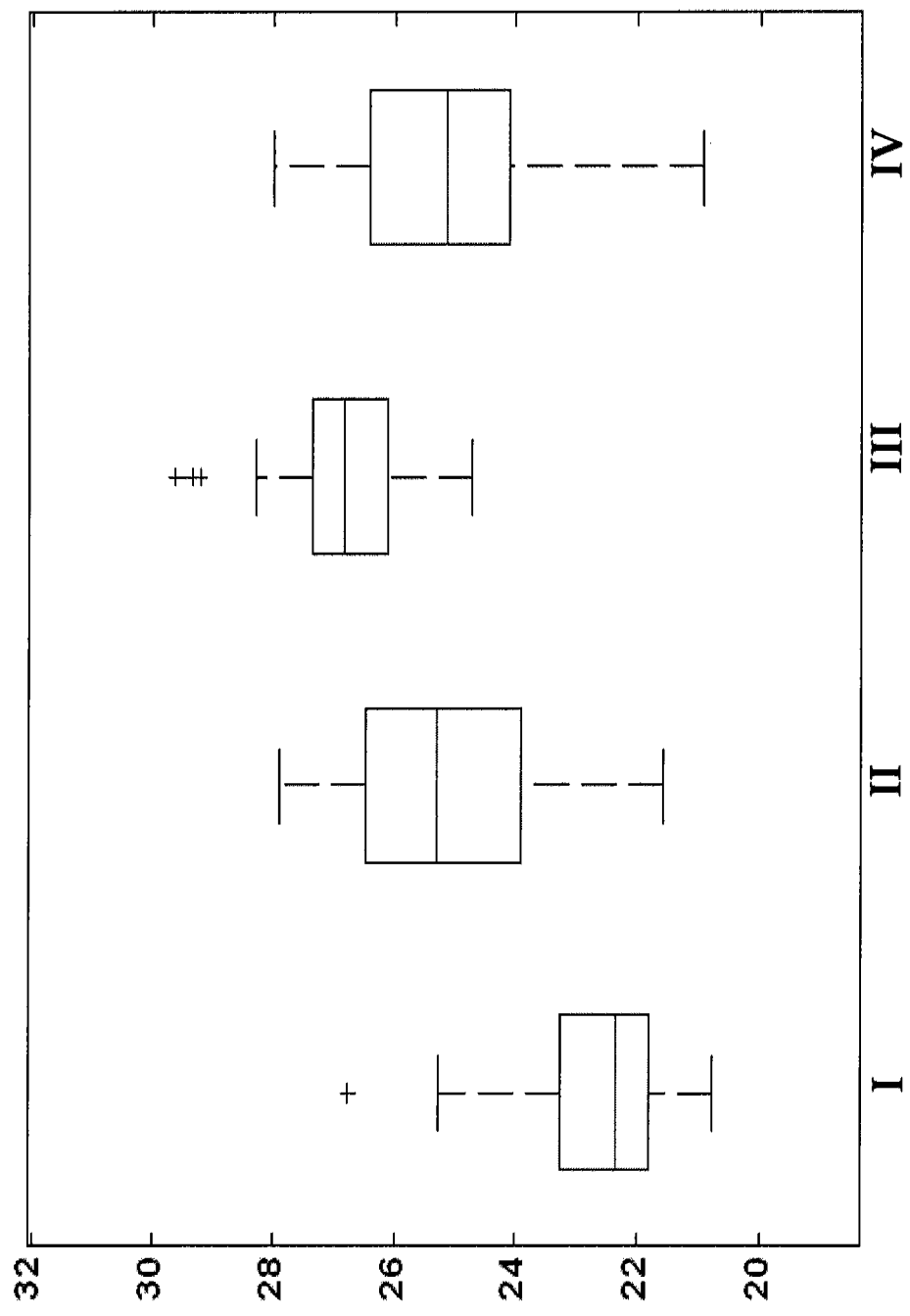
FIG. 7 shows boxplot indicating expression levels of MID-19962 (SEQ ID NO: 11) in 50-Ct units, as measured by PCR obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 8:
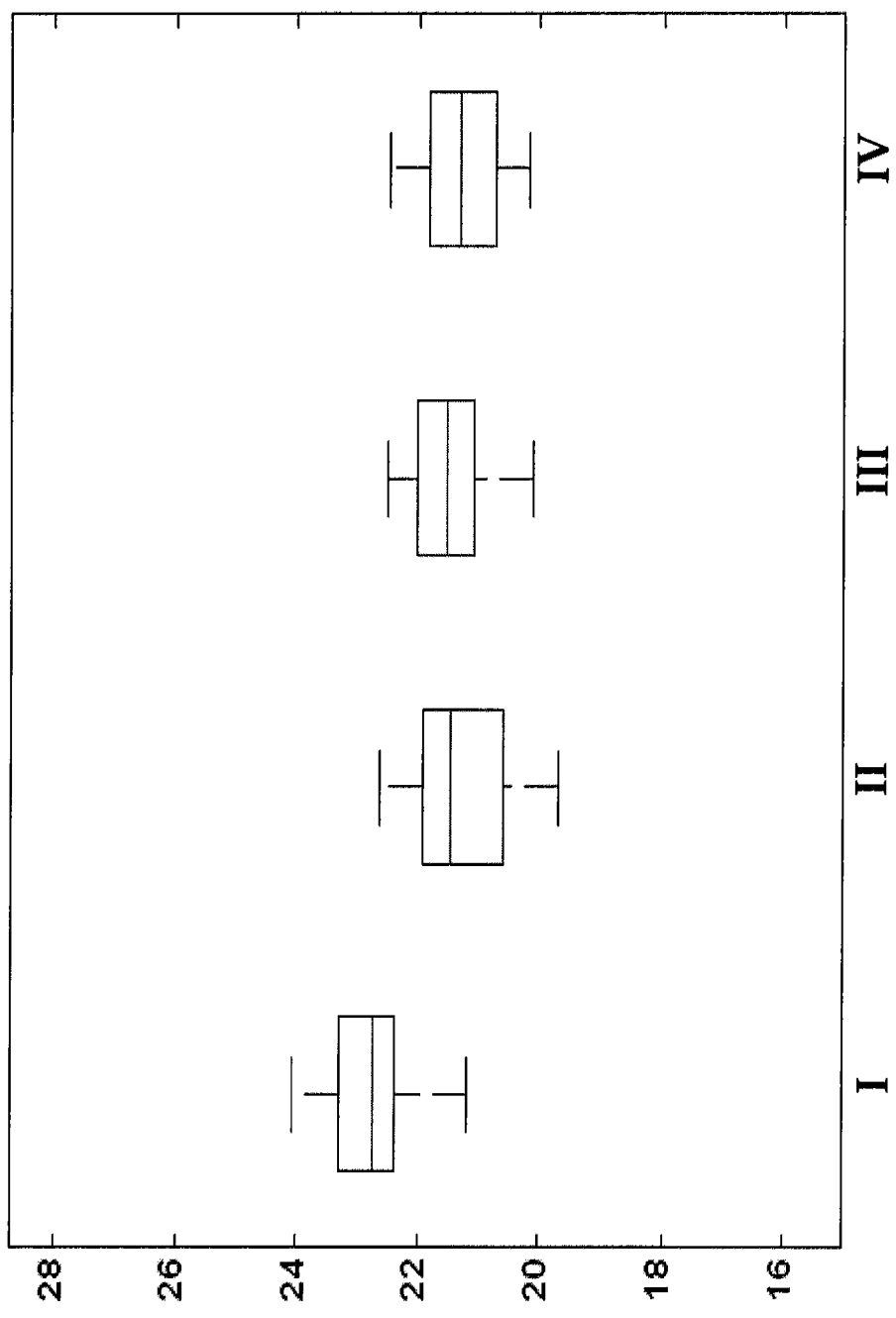
FIG. 8 shows boxplot indicating expression levels of miR-195 (SEQ ID NO: 9) in normalized 50-Ct, as measured by RT-PCR in samples obtained from patients with dear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 9A:
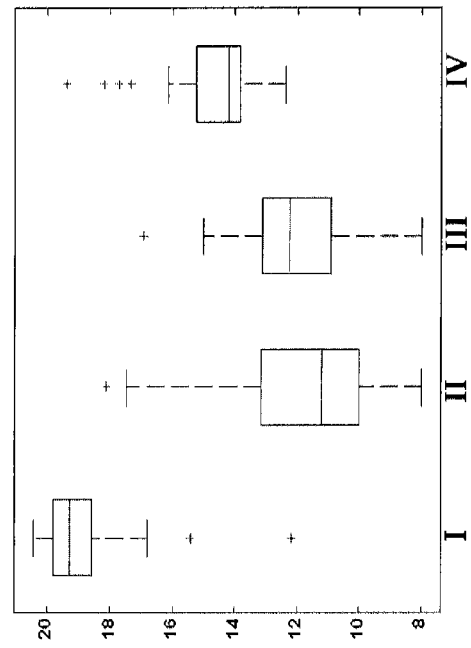
FIGS. 9A-C show boxplots indicating expression levels of miR-221 (SEQ ID NO: 1) (A), miR-122 (SEQ ID NO: 6) (B), and miR-455-3p (SEQ ID NO: 5) (C) in units of (50-Ct), detected by qRT-PCR, in samples obtained from patients with clear cell RCC (I), papillary RCC (II), oncocytoma (III) and chromophobe RCC (IV). Shown are the median value (horizontal line), 25th to 75th percentile (box), extent of data ("whiskers") and outliers (crosses).
Figure 9B:
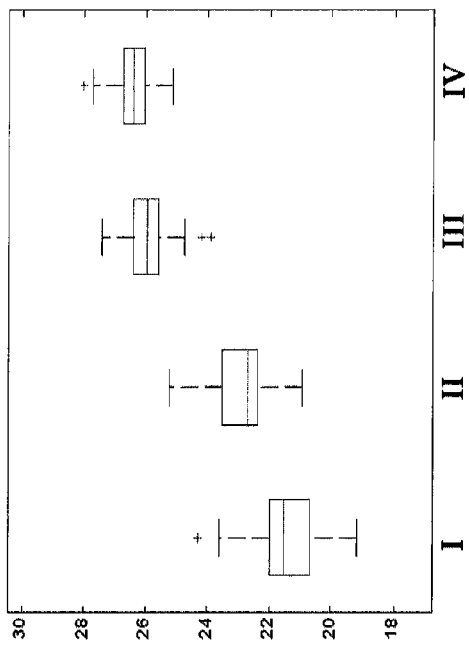
Figure 9C:
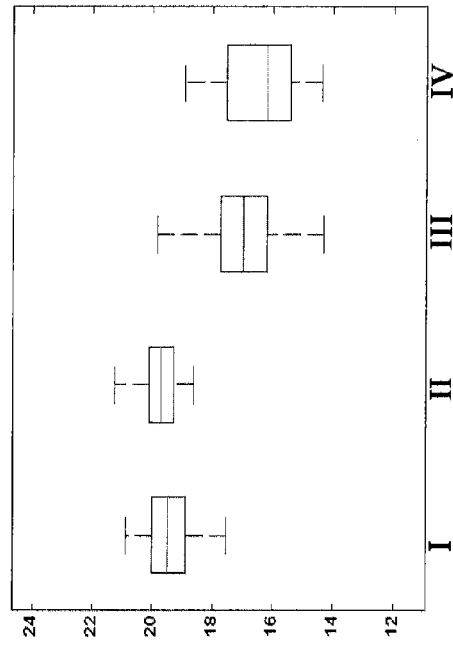

The invention is based in part on the discovery that specific nucleic acid sequences (SEQ ID NOS: 1-24) can be used for the classification of kidney tumors. The present invention provides a sensitive, specific and accurate method which can be used to distinguish between particular subtypes of kidney tumors.

Renal cell cancer comprise of different subtypes of cancers that differ in genetic background, response to surgical and medical therapy and prognosis. The different histological subclasses of RCC are associated with the different disease specific survival that range from 24% to 100% at 5 years from surgery. While non conventional types RCC have a lower pathological stage and reduced portion of metastatic disease, its response to systemic medical therapy is reduced compared to conventional type RCC. Various markers have been suggested and used for this distinction between histology subtypes, but these show mixed or limited specificities, and a significant fraction of samples may be unclassified or misclassified. Unclassified RCC comprise of up to 6% of all RCC even in series from centers of excellence and have the worst clinical outcome as compared to other subclasses. One can assume that the proportion of unclassified RCC is higher in centers lacking dedicated pathologists focusing in genitourinary malignancies and therefore emphasizes that need for additional diagnostic tools for RCC subclassification.

The possibility to distinguish between different subtypes of kidney tumors facilitates providing the patient with the best and most suitable treatment.

The present invention provides diagnostic assays and methods, both quantitative and qualitative for detecting, diagnosing, monitoring, staging and prognosticating kidney cancers by comparing levels of the specific microRNA molecules of the invention. Such levels are preferably measured in at least one of biopsies, tumor samples, cells, tissues and/or bodily fluids. The present invention provides methods for diagnosing the presence of a specific kidney cancer by analyzing the levels of said microRNA molecules in biopsies, tumor samples, cells, tissues or bodily fluids.

In the present invention, determining the levels of said microRNAs in biopsies, tumor samples, cells, tissues or bodily fluid, is particularly useful for discriminating between different subtypes of kidney tumors.

All the methods of the present invention may optionally further include measuring levels of other cancer markers. Other cancer markers, in addition to said microRNA molecules, useful in the present invention will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, but are not limited to, radioimmunoassays, reverse transcriptase PCR (RT-PCR) assays, immunohistochemistry assays, in situ hybridization assays, competitive-binding assays, Northern Blot analyses, ELISA assays, nucleic acid microarrays and biochip analysis.

An arbitrary threshold on the expression level of one or more nucleic acid sequences can be set for assigning a sample or tumor sample to one of two groups. Alternatively, in a preferred embodiment, expression levels of one or more nucleic acid sequences of the invention are combined by taking ratios of expression levels of two nucleic acid sequences and/or by a method such as logistic regression to define a metric which is then compared to previously measured samples or to a threshold. The threshold for assignment is treated as a parameter, which can be used to quantify the confidence with which samples are assigned to each class. The threshold for assignment can be scaled to favor sensitivity or specificity, depending on the clinical scenario. The correlation value to the reference data generates a continuous score that can be scaled and provides diagnostic information on the likelihood that a samples belongs to a certain class of renal subtype. In multivariate analysis, the microRNA signature provides a high level of prognostic information.

DEFINITIONS

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Attached

"Attached" or "immobilized" as used herein to refer to a probe and a solid support means that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, blood fraction, plasma, serum, sputum, stool, tears, mucus, hair, skin, urine, effusions, ascitic fluid, amniotic fluid, saliva, cerebrospinal fluid, cervical secretions, vaginal secretions, endometrial secretions, gastrointestinal secretions, bronchial secretions, cell line, tissue sample, or secretions from the breast. A biological sample may be provided by removing a sample of cells from a subject but can also be accomplished by using previously isolated cells (e.g., isolated by another person, at another time, and/or for another purpose), or by performing the methods described herein in vivo. Archival tissues, such as those having treatment or outcome history, may also be used. Biological samples also include explants and primary and/or transformed cell cultures derived from animal or human tissues.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are not limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, clear cell RCC, papillary RCC and chromophobe RCC, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

The term classification refers to a procedure and/or algorithm in which individual items are placed into groups or classes based on quantitative information on one or more characteristics inherent in the items (referred to as traits, variables, characters, features, etc) and based on a statistical model and/or a training set of previously labeled items.

Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary means 100% complementary base pairing between nucleotides or nucleotide analogs of nucleic acid molecules. In some embodiments, the complementary sequence has a reverse orientation (5'-3').

$C_T$ $C_T$ signals represent the first cycle of PCR where amplification crosses a threshold (cycle threshold) of fluorescence. Accordingly, low values of $C_T$ represent high abundance or expression levels of the microRNA.

In some embodiments the PCR $C_T$ signal is normalized such that the normalized $C_T$ remains inversed from the expression level. In other embodiments the PCR $C_T$ signal may be normalized and then inverted such that low normalized-inverted $C_T$ represents low abundance or expression levels of the microRNA.

Data Processing Routine

As used herein, a "data processing routine" refers to a process that can be embodied in software that determines the biological significance of acquired data (i.e., the ultimate results of an assay or analysis). For example, the data processing routine can make determination of tissue of origin based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

Data Set

As use herein, the term "data set" refers to numerical values obtained from the analysis. These numerical values associated with analysis may be values such as peak height and area under the curve.

Data Structure

As used herein the term "data structure" refers to a combination of two or more data sets, applying one or more mathematical manipulations to one or more data sets to obtain one or more new data sets, or manipulating two or more data sets into a form that provides a visual illustration of the data in a new way. An example of a data structure prepared from manipulation of two or more data sets would be a hierarchical cluster.

Detection

"Detection" means detecting the presence of a component in a sample. Detection also means detecting the absence of a component. Detection also means determining the level of a component, either quantitatively or qualitatively.

Differential Expression

"Differential expression" means qualitative or quantitative differences in the temporal and/or spatial gene expression patterns within and among cells and tissue. Thus, a differentially expressed gene may qualitatively have its expression altered, including an activation or inactivation, in, e.g., normal versus diseased tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs needs only be large enough to quantify via standard characterization techniques such as expression arrays, quantitative reverse transcriptase PCR, Northern blot analysis, real-time PCR, in situ hybridization and RNase protection.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cDNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. According to some embodiments, the term "expression profile" means measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR (False Discovery Rate)

When performing multiple statistical tests, for example in comparing between the signal of two groups in multiple data features, there is an increasingly high probability of obtaining false positive results, by random differences between the groups that can reach levels that would otherwise be considered statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA sequences, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

K-nearest Neighbor

The phrase "K-nearest neighbor" refers to a classification method that classifies a point by calculating the distances between it and points in the training data set. It then assigns the point to the class that is most common among its K-nearest neighbors (where K is an integer).

Label

"Label" as used herein means a composition detectable by spectroscopic, photochemical, biochemical, immunochemical, chemical, or other physical means. For example, useful labels include $P^{32}$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression can allow one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e., the ratio of the probability of belonging to the first group (P) over the probability of belonging to the second group (1−P), as a linear combination of the different expression levels (in log-space). The logistic regression output can be used as a classifier by prescribing that a case or sample will be classified into the first type if P is greater than 0.5 or 50%. Alternatively, the calculated probability P can be used as a variable in other contexts, such as a 1D or 2D threshold classifier.

1D/2D Threshold Classifier

"1D/2D threshold classifier" used herein may mean an algorithm for classifying a case or sample such as a cancer sample into one of two possible types such as two types of cancer. For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A threshold may be calculated as a function (usually a continuous or even a monotonic function) of the first variable; the decision is then reached by comparing the second variable to the calculated threshold, similar to the 1D threshold classifier.

Nucleic Acid

"Nucleic acid" or "oligonucleotide" or "polynucleotide", as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated herein by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, NH2, NHR, NR2 or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Reference Value

As used herein the term "reference value" means a value that statistically correlates to a particular outcome when compared to an assay result. In preferred embodiments the reference value is determined from statistical analysis of studies that compare microRNA expression with known clinical outcomes.

Sensitivity

"sensitivity" used herein may mean a statistical measure of how well a classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Specificity

"Specificity" used herein may mean a statistical measure of how well a classification test correctly identifies a condition, for example how frequently it correctly classifies a cancer into the correct type out of two possible types. The specificity for class A is the proportion of cases that are determined to belong to class "not A" by the test out of the cases that are in class "not A", as determined by some absolute or gold standard.

Stage of Cancer

As used herein, the term "stage of cancer" refers to a numerical measurement of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subtype of Cancer

As used herein, the term "subtype of cancer" refers to different types of cancer that effect the same organ (e.g., spindle cell, cystic and collecting duct carcinomas of the kidney).

Subject

As used herein, the term "subject" refers to a mammal, including both human and other mammals. The methods of the present invention are preferably applied to human subjects.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Threshold Expression Profile

As used herein, the phrase "threshold expression profile" refers to a criterion expression profile to which measured values are compared in order to classify a tumor.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Tumor

"Tumor" as used herein, refers to all neoplastic cell growth and proliferation, whether malignant or benign, and all pre-cancerous and cancerous cells and tissues.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNAs for the identification, classification and diagnosis of specific cancers and the identification of their tissues of origin.

microRNA Processing

A gene coding for microRNA (miRNA) may be transcribed leading to production of a miRNA primary transcript known as the pri-miRNA. The pri-miRNA may comprise a hairpin with a stem and loop structure. The stem of the hairpin may comprise mismatched bases. The pri-miRNA may comprise several hairpins in a polycistronic structure.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acids comprise the sequences of SEQ ID NOS: 1-81 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from about 10 to about 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

TABLE 1

The nucleic acids of the invention (miRs and hairpins)

| miR name | miR SEQ ID No. | hairpin SEQ ID No. |
|---|---|---|
| hsa-miR-221 | 1 | 25 |
| hsa-miR-222 | 2 | 26 |
| hsa-miR-210 | 3 | 27 |
| hsa-miR-21 | 4 | 28 |
| hsa-miR-455-3p | 5 | 29 |
| hsa-miR-122 | 6 | 30 |
| hsa-miR-126 | 7 | 31 |
| hsa-miR-31 | 8 | 32 |
| hsa-miR-195 | 9 | 33 |
| hsa-miR-182 | 10 | 34 |
| MID-19962 | 11 | 35 and 36 |
| hsa-miR-139-5p | 12 | 37 |
| hsa-miR-200c | 13 | 38 |
| hsa-miR-141 | 14 | 39 |
| hsa-miR-200b | 15 | 40 |
| hsa-miR-551b | 16 | 41 |
| hsa-miR-200a | 17 | 42 |
| MID-16582 | 18 | 45 and 46 |
| hsa-miR-130a | 19 | 43 |
| hsa-miR-93 | 20 | 44 |
| MID-16869 | 21 | 47 |
| hsa-miR-146a | 22 | 48 |
| MID-00536 | 23 | 49 |
| hsa-miR-192 | 24 | 51 | miR name: is the miRBase registry name (release 15)

MID-19962, MID-00536, MID-16869 and MID-16582 are not presented in the miRBase registry. They were cloned in Rosetta Genomics.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000,100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise any of the sequences of SEQ ID NOS: 1-51 or variants thereof.

The pri-miRNA may comprise a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole as calculated by the Vienna algorithm with default parameters, as described in Hofacker et al., Monatshefte f. Chemie 125: 167-188 (1994), the contents of which are incorporated herein by reference. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-51, or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-24, or variants thereof.

Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 67-81, or variants thereof.

Linker Sequences

The probe may further comprise a linker. The linker may be 10-60 nucleotides in length.

The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides. The forward primer may comprise SEQ ID NOS: 52-66; or variants thereof.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise SEQ ID NO: 82 (GCGAGCACAGAATTAATACGAC) or variants thereof.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostics

As used herein the term "diagnosing" refers to classifying pathology, or a symptom, determining a severity of the pathology (e.g., grade or stage), monitoring pathology progression, forecasting an outcome of pathology and/or prospects of recovery.

As used herein the phrase "subject in need thereof" refers to an animal or human subject who is known to have cancer, at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

Analyzing presence of malignant or pre-malignant cells can be effected in-vivo or ex-vivo, whereby a biological sample (e.g., biopsy) is retrieved. Such biopsy samples comprise cells and may be an incisional or excisional biopsy. Alternatively the cells may be retrieved from a complete resection.

While employing the present teachings, additional information may be gleaned pertaining to the determination of treatment regimen, treatment course and/or to the measurement of the severity of the disease.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

A method of diagnosis is also provided. The method comprises detecting an expression level of a specific cancer-associated nucleic acid in a biological sample. The sample may be derived from a patient. Diagnosis of a specific cancer state in a patient may allow for prognosis and selection of therapeutic strategy. Further, the developmental stage of cells may be classified by determining temporarily expressed specific cancer-associated nucleic acids.

In situ hybridization of labeled probes to tissue sections may be performed. When comparing the fingerprints between individual samples the skilled artisan can make a diagnosis, a prognosis, or a prediction based on the findings. It is further understood that the nucleic acid sequence which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. The kit may further comprise a software package for data analysis of expression profiles.

For example, the kit may be a kit for the amplification, detection, identification or quantification of a target nucleic acid sequence. The kit may comprise a poly (T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

The following examples are presented in order to more fully illustrate some embodiments of the invention. They should, in no way be construed, however, as limiting the broad scope of the invention.

EXAMPLES

Materials and Methods
1. Tumor Samples

Renal tumor FFPE samples were obtained from the pathology archives of Sheba Medical Center (Tel-Hashomer, Israel) and commercial sources (ABS Inc., Wilmington, Del., and BioServe™, Beltsville, Md.). The study protocol was approved by the Research Ethics Board of each of the contributing institutes. FFPE samples were reviewed by a second pathologist prior to their inclusion in the study for histological type based on hematoxylin-eosin (H&E) stained slides, performed on the first and/or last sections of the sample. Tumor classification was based on the World Health Organization (WHO) guidelines. Tumor content was higher than 60% for all the samples and higher than 80% for >80% of the samples.

2. RNA Extraction

Total RNA was isolated as previously described (Rosenfeld et al., 2008). Briefly, three to ten 10 μm-thick tissue sections were incubated a few times in xylene at 57 °C. to remove excess paraffin, and then washed several times with ethanol. Proteins were degraded by incubating the sample in a proteinase K solution at 45 °C. for a few hours. RNA was extracted using acid phenol/chloroform and then precipitated using ethanol; DNAses were introduced to digest DNA. Total RNA quantity and quality was measured by NANODROP™ ND-1000 (NanoDrop Technologies, Wilmington, Del.).

3. MicroRNA Profiling-HM

Custom microarrays were produced by printing DNA oligonucleotide probes to more than 900 human microRNAs. Each probe, printed in triplicate, carries up to 22-nucleotide (nt) linker at the 3' end of the microRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides using a Genomic Solutions® BioRobotics MicroGrid II according the MicroGrid manufacturer's directions. 54 negative control probes were designed using the sense sequences of different microRNAs. Two groups of positive control probes were designed to hybridize to microarray (i) synthetic small RNA were spiked to the RNA before labeling to verify the labeling efficiency and (ii) probes for abundant small RNA (e.g. small nuclear RNAs (U43, U49, U24, Z30, U6, U48, U44), 5.8s and 5s ribosomal RNA) were spotted on the array to verify RNA quality. The slides were blocked in a solution containing 50 mM ethanolamine, 1M Tris (pH9.0) and 0.1% SDS for 20 min at 50° C., then thoroughly rinsed with water and spun dry.

4. Cy-dye Labeling of miRNA for Microarray 3.5 μg of total RNA were labeled by ligation (Thomson et al., Nature Methods 2004, 1:47-53) of an RNA-linker, p-rCrU-Cy/dye (Dharmacon), to the 3'-end with Cy3 or Cy5. The labeling reaction contained total RNA, spikes (0.1-20 fmoles), 300 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and than added on top of the miRdicator™ array. Slides were hybridized 12-16 hr in 42° C., followed by two washes in room temperature with 1×SSC and 0.2% SDS and a final wash with 0.1×SSC.

Arrays were scanned using an Agilent Microarray Scanner Bundle G2565BA (resolution of 10 μm, scanning mode dual Pass, PMT XDR Hi 100% and XDR Lo 10%). Array images were analyzed using SpotReader software (Niles Scientific).

5. Array Data Normalization

The initial data set consisted of signals measured for multiple probes for every sample. For the analysis, signals were used only for probes that were designed to measure the expression levels of known or validated human microRNAs.

Triplicate spots were combined into one signal by taking the logarithmic mean of the reliable spots. All data was log-transformed and the analysis was performed in log-space. A reference data vector for normalization, R, was calculated by taking the mean expression level for each probe in two representative samples, one from each tumor type.

For each sample k with data vector $S^k$, a 2nd degree polynomial $F^k$ was found so as to provide the best fit between the sample data and the reference data, such that $R \approx F^k(S^k)$. Remote data points ("outliers") were not used for fitting the polynomials F. For each probe in the sample (element $S_i^k$ in the vector $S^k$), the normalized value (in log-space) $M_i^k$ is calculated from the initial value $S_i^k$ by transforming it with the polynomial function $F^k$, so that $M_i^k = F^k(S_i^k)$. Statistical analysis is performed in log-space. For presentation and calculation of fold-change, data is translated back to linear-space by taking the exponent.

6. miR Array Platform—Agilent 181 tumor samples were used for array analysis. Custom microarrays (Agilent Technologies, Santa Clara, Calif.) were produced by printing DNA oligonucleotide probes to: 982 miRs sequences, 18 negative controls, 23 spikes, and 10 positive controls (total of 1033 probes). Each probe, printed in triplicate, carried up to 27-nucleotide (nt) linker at the 3' end of the microRNA's complement sequence. 17 negative control probes were designed using as sequences which do not match the genome. Two groups of positive control probes were designed to hybridize to miR array: (i) synthetic small RNAs were spiked to the RNA before labeling to verify the labeling efficiency; and (ii) probes for abundant small RNA (e.g., small nuclear RNAs (U43, U49, U24, Z30, U6, U48, U44), 5.8s and 5s ribosomal RNA) are spotted on the array to verify RNA quality.

7. Cy-dye Labeling of miRNA for miR Agilent Array

1 µg of total RNA was labeled by ligation (Thomson et al. Nature Methods 2004; 1:47-53) of an RNA-linker, p-rCrU-Cy/dye (Eurogentec or eqvivalent), to the 3' end with Cy3 or Cy5. The labeling reaction contained total RNA, spikes (0.1-20 fmoles), 400 ng RNA-linker-dye, 15% DMSO, 1× ligase buffer and 20 units of T4 RNA ligase (NEB), and proceeded at 4° C. for 1 h, followed by 1 h at 37° C. Every two labeled RNAs labelead with different Dys was mixed together with 1.25×Hi-RMP hybridization buffer (Agilent), heated to 100° C. for 5 min. After incubate the tubes on ice for 5 min the mixture added on top of the miR array. Slides were hybridized for 12-16 h at 55° C., followed by two washes at room temperature with 1×SSC and 0.2% SDS and a final wash with 0.1×SSC.

Arrays were scanned using an Agilent Microarray Scanner Bundle G2565BA. Arrays were scanned at a resolution of 10 µm, scanning mode dual Pass, PMT XDR Hi 100% and XDR Lo 10%. Array images were analyzed using SpotReader software (Niles Scientific).

8. Array Signal Calculation and Normalization

Triplicate spots were combined to produce one signal for each probe by taking the logarithmic mean of reliable spots. All data were log-transformed and the analysis was performed in log-space. A reference data vector for normalization R was calculated by taking the median expression level for each probe across all samples (See details in section 5).

9. Statistical Analysis

Figure 10:
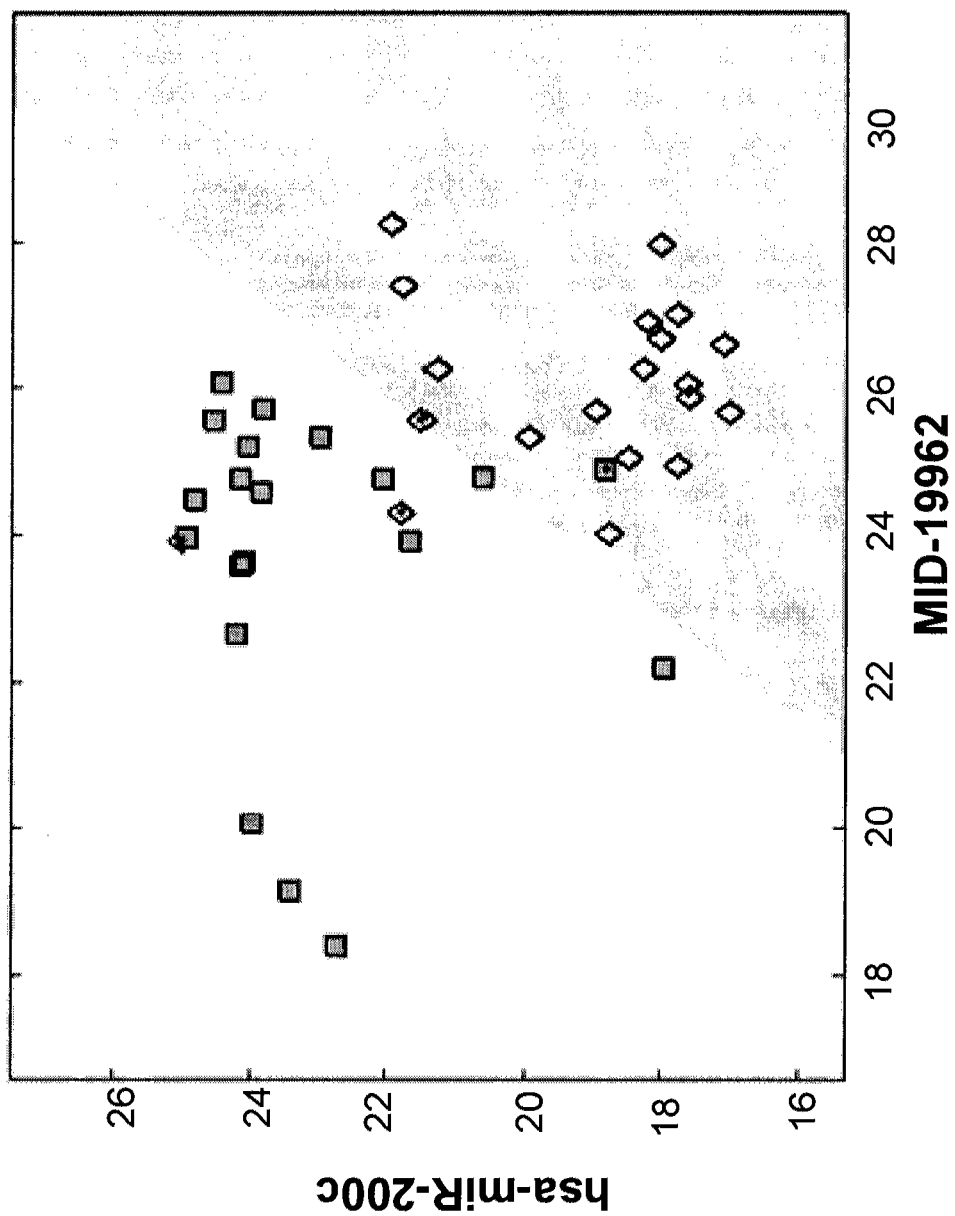
FIG. 10 demonstrates separation between oncocytoma samples (diamonds) and chromophobe tumors (squares) using expression levels of hsa-miR-200c (SEQ ID NO: 13) and MID-19962 (SEQ ID NO: 11) as detected by qRT-PCR (50-$C_T$). The grey regions indicate the thresholds for classification.
Figure 11:
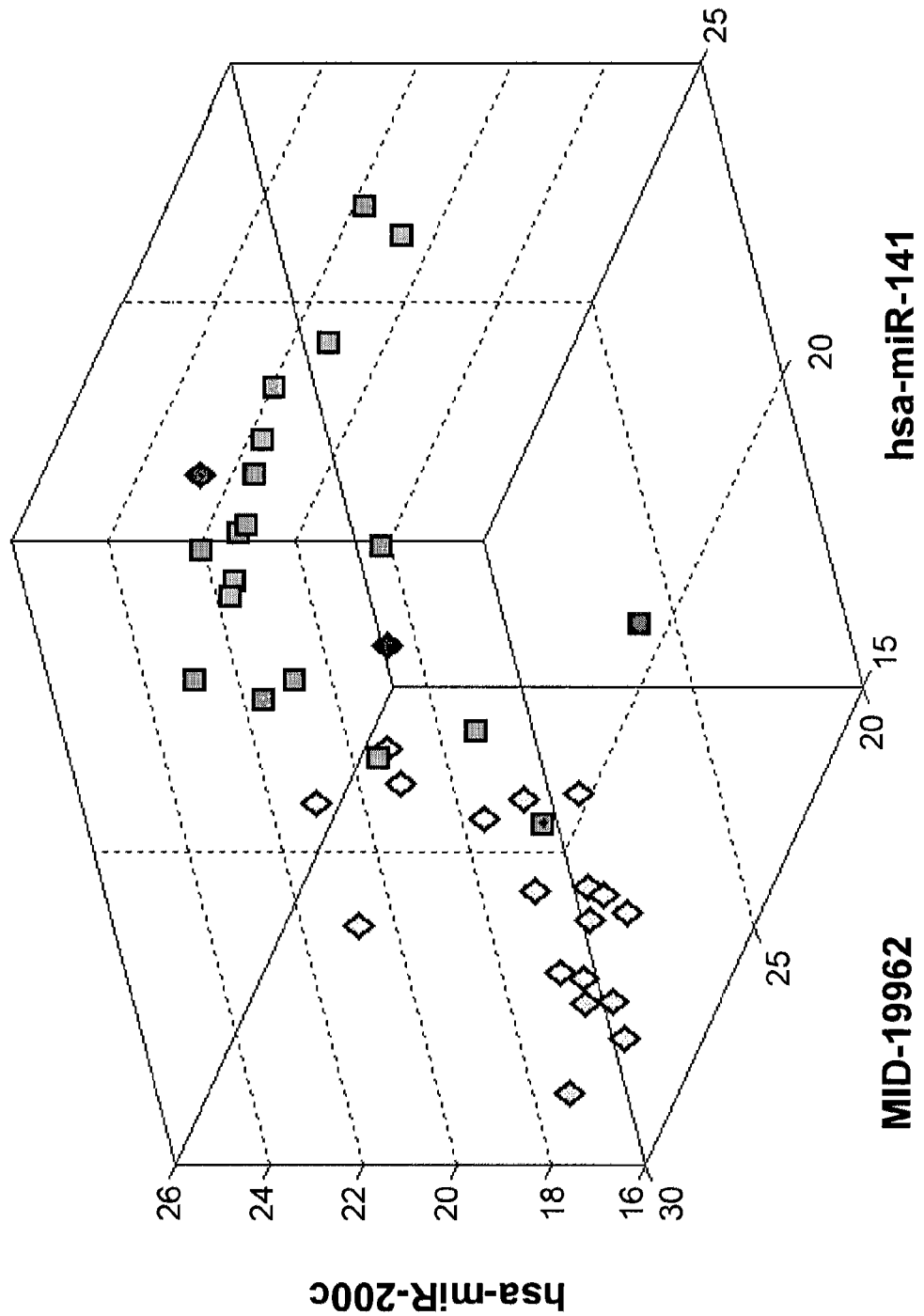
FIG. 11 demonstrates separation between oncocytoma samples (diamonds) and chromophobe tumors (squares), using expression levels of hsa-miR-141 (SEQ ID NO: 14), MID-19962 (SEQ ID NO: 11) and hsa-miR-200c (SEQ ID NO: 13) as detected by qRT-PCR (50-$C_T$).
Figure 12:
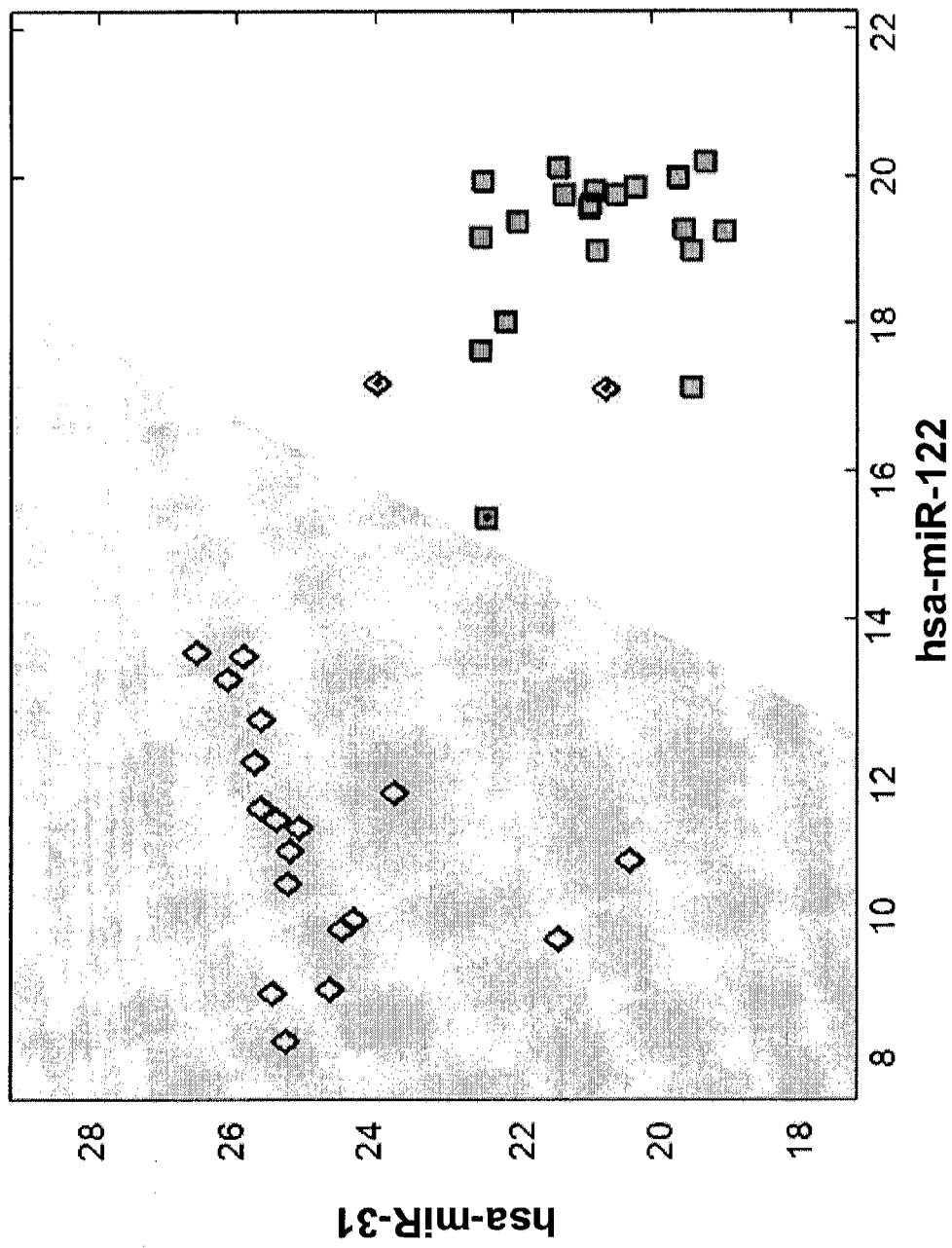
FIG. 12 demonstrates separation between papillary tumors (diamonds) and clear cell tumors (squares) using expression levels of hsa-miR-122 (SEQ ID NO: 6) and hsa-miR-31 (SEQ ID NO: 8) as detected by qRT-PCR (50-$C_T$). The grey regions indicate the thresholds for classification.

For every pair of groups (e.g., oncocytoma vs. chromophobe or Clear cell vs. papillary), microRNA expression was compared for all microRNAs that had expression level above background (median normalized fluorescence signal>700) in at least one of the two groups. P-values were calculated using either a two-sided (unpaired) Student's t-test on the log-transformed normalized fluorescence signal or a rank sum test on log-transformed normalized data. The threshold for significant differences was determined by setting a False Discovery Rate (FDR) of 0.1, to correct for effects of multiple hypothesis testing. For each differentially expressed microRNA we calculated the fold-difference (ratio of the median normalized fluorescence) and the area under curve (AUC) of the response operating characteristic (ROC) curve. For classification, sub sets of the differential miRs were tested for their ability to classify the renal sub classes using different classifiers such as decision tree using linear regression or KNN. In some embodiments two to three microRNAs with opposite specificity were chosen at each decision point, and linear separator based on linear combination of those miRs expression was calculated (indicated by the grey shaded regions in FIGS. 10 and 12). These separators were used to classify the test samples.

10. RT-PCR 134 tumor samples were used for RT-PCR analysis. RNA was incubated in the presence of poly (A) polymerase (Poly (A) Polymerase NEB-Mo276L), MnClz, and ATP for 1 hour at 37° C. Then, using an oligodT primer harboring a consensus sequence, reverse transcription was performed on total RNA using SUPERSCRIPT® II RT (Invitrogen, Carlsbad, Calif.). Next, the cDNA was amplified by RT-PCR; this reaction contained a microRNA-specific forward primer, a TAQ-MAN® (MGB) probe complementary to the 3' of the specific microRNA sequence as well as to part of the polyA adaptor sequence, and a universal reverse primer complementary to the consensus 3' sequence of the oligodT tail (Table 2).

The cycle threshold ($C_T$, the PCR cycle at which probe signal reaches the threshold) was determined for each microRNA. To allow comparison with results from the microarray, each value received was subtracted from 50. This 50-$C_T$ expression for each microRNA for each patient was compared with the signal obtained by the microarray method.

11. K-nearest-neighbors (KNN) Classification Algorithm

The KNN algorithm (see e.g., Ma et al., Arch Pathol Lab Med 2006; 130:465-73) calculates the distance (Pearson correlation) of any sample to all samples in the training set, and classifies the sample by the majority vote of the k samples which are most similar (k being a parameter of the classifier). The distance is calculated on the pre-defined set of microRNAs (SEQ ID NOS 1-24). KNN algorithms with k=1;10 were compared, and the optimal performer was selected, using k=5. The KNN was based on comparing the expression of all 24 microRNAs in each sample to all other samples in the training database.

TABLE 2

Sequences used in RT-PCR

| miR name | FWD Sequence | FWD SEQ ID No: | MGB Sequence | MGB SEQ ID No: |
| --- | --- | --- | --- | --- |
| has-miR-222 | CAGTCATTTGGGAGCTACATCTGGCTAC | 52 | ATCCGTTTTTTTTTTTACCCAGTA | 67 |
| has-miR-200b | CAGTCATTTGGGTAATACTGCCTGGTAA | 53 | CCGTTTTTTTTTTTCATCATTA | 68 |
| has-miR-21 | CAGTCATTTGGCTAGCTTATCAGACTGA | 54 | CCGTTTTTTTTTTTCAACATCA | 69 |
| has-miR-210 | CAGTCATTTGGGCTGTGCGTGTGACAGC | 55 | CGTTTTTTTTTTTCAGCCGCT | 70 |
| has-miR-221 | CAGTCATTTGGGAGCTACATTGTCTGCT | 56 | CGTTTTTTTTTTTGAAACCCA | 71 |
| has-miR-182 | CAGTCATTTGGGTTTGGCAATGGTAGAA | 57 | TCCGTTTTTTTTTTTAGTGTGAG | 72 |
| has-miR-139-5p | GGCTCTACAGTGCACGTGTCT | 58 | AAAACCGATAGTGAGTCG | 73 |
| has-miR-126 | CAGTCATTTGGGTCGTACCGTGAGTAAT | 59 | CCGTTTTTTTTTTTCGCATTAT | 74 |
| has-miR-195 | CAGTCATTTGGCTAGCAGCACAGAAATA | 60 | CCGTTTTTTTTTTTGCCAATAT | 75 |
| has-miR-455-3p | CAGTCATTTGGCGCAGTCCATGGGCATA | 61 | CCGTTTTTTTTTTTGTGTATAT | 76 |

TABLE 2-continued

Sequences used in RT-PCR

| miR name | FWD Sequence | FWD SEQ ID No: | MGB Sequence | MGB SEQ ID No: |
|---|---|---|---|---|
| has-miR-122 | CAGTCATTTGGGTGGAGTGTGACAATGG | 62 | CGTTTTTTTTTTTCAAACACC | 77 |
| has-miR-31-Gen | AGGCAAGATGCTGGCATAGCT | 63 | AAAACCGATAGTGAGTCG | 78 |
| MID-19962-Gen | CAGTCATTTGGCTAAAAGGAACTCGGCA | 64 | CCGTTTTTTTTTTTATTTGCCG | 79 |
| has-miR-200c | CAGTCATTTGGGTAATACTGCCGGGTAA | 65 | CGTTTTTTTTTTTTCCATCATT | 80 |
| has-miR-141 | CAGTCATTTGGGTAACACTGTCTGGTAA | 66 | CGTTTTTTTTTTTTCCATCTTT | 81 |
| Reverse primer | GCGAGCACAGAATTAATACGAC | 82 | | |

Example 1

Specific microRNAs Detected by Microarray are Able to Distinguish Between Different Subtypes of Renal Tumor Samples The microarray performed as described in the "Materials and Methods" section identified multiple miRs that were significantly differentially expressed between 181 tumors from patients diagnosed with oncocytoma, clear cell RCC, papillary RCC and chromophobe RCC as demonstrated in FIGS. 1-6. These miRs are presented in Table 3.

TABLE 3 miR expression as measured by a microarray (in florescence units) distinguishing between different subtypes of renal tumor samples

| | Clear Vs Papillary | | | | Clear Vs Oncocytoma | | | |
|---|---|---|---|---|---|---|---|---|
| miR name | Mean 1 | Mean 2 | fold | pVal | Mean 1 | Mean 2 | fold | pVal |
| hsa-miR-221 | 12.27 | 12.94 | 1.59 | 1.20E−05 | 12.27 | 15.89 | 12.34 | 1.10E−36 |
| hsa-miR-222 | 12.93 | 13.32 | 1.31 | 1.20E−02 | 12.93 | 15.8 | 7.3 | 7.60E−32 |
| hsa-miR-210 | 13.45 | 12.19 | 2.39 | 1.70E−10 | 13.45 | 9.59 | 14.49 | 1.70E−37 |
| hsa-miR-21 | 15.63 | 16.61 | 1.97 | 3.20E−12 | 15.63 | 13.57 | 4.19 | 4.70E−18 |
| hsa-miR-455-3p | 10.95 | 10.69 | 1.19 | 1.50E−01 | 10.95 | 8.54 | 5.31 | 5.90E−20 |
| hsa-miR-122 | 8.63 | 5.64 | 7.92 | 1.50E−32 | 8.63 | 5.64 | 7.92 | 8.80E−27 |
| hsa-miR-126 | 13.94 | 11.06 | 7.39 | 3.40E−36 | 13.94 | 13.63 | 1.24 | 4.20E−02 |
| hsa-miR-31 | 9.29 | 13.59 | 19.6 | 1.40E−25 | 9.29 | 8.06 | 2.35 | 9.50E−04 |
| hsa-miR-195 | 12.36 | 10.49 | 3.65 | 1.00E−16 | 12.36 | 11.3 | 2.09 | 3.70E−08 |
| hsa-miR-182 | 6.72 | 9.16 | 5.43 | 1.90E−19 | 6.72 | 10.1 | 10.43 | 4.70E−25 |
| MID-19962 | 10.04 | 11.55 | 2.84 | 2.10E−07 | 10.04 | 13.19 | 8.9 | 1.10E−24 |
| hsa-miR-139-5p | 8.59 | 6.75 | 3.58 | 1.90E−15 | 8.59 | 10.44 | 3.6 | 1.90E−12 |
| hsa-miR-200c | 7.28 | 8 | NaN | NaN | 7.28 | 8.34 | NaN | NaN |
| hsa-miR-141 | 6.35 | 6.62 | NaN | NaN | 6.35 | 7.25 | NaN | NaN |
| hsa-miR-200b | 10.86 | 13.48 | 6.15 | 3.40E−20 | 10.86 | 10.76 | 1.08 | 7.50E−01 |
| hsa-miR-551b | 6.6 | 9.15 | 5.84 | 2.40E−18 | 6.6 | 9.24 | 6.24 | 1.10E−14 |
| hsa-miR-200a | 10.56 | 12.71 | 4.41 | 4.80E−18 | 10.56 | 10.25 | 1.25 | 3.00E−01 |
| MID-16582 | 14.42 | 15.05 | 1.55 | 2.90E−03 | 14.42 | 17.05 | 6.19 | 1.70E−21 |
| hsa-miR-130a | 11.67 | 11.71 | 1.03 | 7.20E−01 | 11.67 | 11.31 | 1.29 | 1.50E−03 |
| hsa-miR-93 | 12.05 | 12.57 | 1.43 | 3.60E−05 | 12.05 | 11.07 | 1.97 | 2.20E−11 |
| MID-16869 | 9.53 | 10.14 | 1.52 | 6.50E−02 | 9.53 | 9.42 | 1.08 | 7.50E−01 |
| hsa-miR-146a | 10.08 | 10.51 | 1.35 | 1.50E−02 | 10.08 | 8.25 | 3.55 | 1.20E−18 |
| MID-00536 | 11.99 | 13.13 | 2.21 | 2.10E−08 | 11.99 | 14.94 | 7.73 | 5.70E−35 |
| hsa-miR-192 | 11.48 | 9.88 | 3.03 | 5.10E−06 | 11.48 | 7.91 | 11.88 | 2.80E−19 |

| | Clear Vs Chromophobe | | | | Papillary Vs Oncocytoma | | | |
|---|---|---|---|---|---|---|---|---|
| MiR name | Mean 1 | Mean 2 | fold | pVal | Mean 1 | Mean 2 | fold | pVal |
| hsa-miR-221 | 12.27 | 16.59 | 20.07 | 1.00E−45 | 12.94 | 15.89 | 7.74 | 4.30E−33 |
| hsa-miR-222 | 12.93 | 16.81 | 14.76 | 1.10E−41 | 13.32 | 15.8 | 5.58 | 1.20E−29 |
| hsa-miR-210 | 13.45 | 9.33 | 17.33 | 3.50E−32 | 12.19 | 9.59 | 6.06 | 8.50E−27 |
| hsa-miR-21 | 15.63 | 13.83 | 3.5 | 3.00E−17 | 16.61 | 13.57 | 8.26 | 2.80E−31 |
| hsa-miR-455-3p | 10.95 | 7.71 | 9.39 | 1.80E−26 | 10.69 | 8.54 | 4.45 | 9.90E−21 |
| hsa-miR-122 | 8.63 | 5.7 | 7.62 | 4.80E−26 | 5.64 | 5.64 | NaN | NaN |
| hsa-miR-126 | 13.94 | 13.01 | 1.91 | 8.20E−08 | 11.06 | 13.63 | 5.94 | 5.10E−28 |
| hsa-miR-31 | 9.29 | 9.46 | 1.12 | 6.90E−01 | 13.59 | 8.06 | 46.05 | 4.60E−30 |
| hsa-miR-195 | 12.36 | 10.63 | 3.31 | 7.80E−16 | 10.49 | 11.3 | 1.75 | 9.10E−05 |

TABLE 3-continued miR expression as measured by a microarray (in florescence units) distinguishing between different subtypes of renal tumor samples

| | | | | | | | | |
|---|---|---|---|---|---|---|---|---|
| hsa-miR-182 | 6.72 | 10.69 | 15.75 | 7.70E−29 | 9.16 | 10.1 | 1.92 | 3.00E−04 |
| MID-19962 | 10.04 | 11.55 | 2.85 | 1.40E−06 | 11.55 | 13.19 | 3.13 | 8.80E−09 |
| hsa-miR-139-5p | 8.59 | 8.51 | 1.06 | 7.00E−01 | 6.75 | 10.44 | 12.89 | 1.60E−34 |
| hsa-miR-200c | 7.28 | 13.49 | 74.36 | 2.40E−33 | 8 | 8.34 | NaN | NaN |
| hsa-miR-141 | 6.35 | 11.82 | 44.45 | 3.20E−34 | 6.62 | 7.25 | NaN | NaN |
| hsa-miR-200b | 10.86 | 13.14 | 4.85 | 2.50E−16 | 13.48 | 10.76 | 6.61 | 2.70E−15 |
| hsa-miR-551b | 6.6 | 6.6 | NaN | NaN | 9.15 | 9.24 | 1.07 | 7.90E−01 |
| hsa-miR-200a | 10.56 | 12.03 | 2.77 | 2.30E−09 | 12.71 | 10.25 | 5.5 | 8.00E−16 |
| MID-16582 | 14.42 | 15.17 | 1.68 | 1.60E−04 | 15.05 | 17.05 | 4 | 2.60E−12 |
| hsa-miR-130a | 11.67 | 10.17 | 2.84 | 4.70E−18 | 11.71 | 11.31 | 1.32 | 1.00E−03 |
| hsa-miR-93 | 12.05 | 11.47 | 1.49 | 4.10E−06 | 12.57 | 11.07 | 2.82 | 1.50E−18 |
| MID-16869 | 9.53 | 11.18 | 3.12 | 5.10E−06 | 10.14 | 9.42 | 1.65 | 3.20E−02 |
| hsa-miR-146a | 10.08 | 8.35 | 3.32 | 1.00E−17 | 10.51 | 8.25 | 4.78 | 2.50E−21 |
| MID-00536 | 11.99 | 14.03 | 4.13 | 8.50E−21 | 13.13 | 14.94 | 3.49 | 3.70E−15 |
| hsa-miR-192 | 11.48 | 8.35 | 8.8 | 9.70E−17 | 9.88 | 7.91 | 3.92 | 2.00E−07 |

| | Papillary Vs Chromophobe | | | | Oncocytoma Vs Chromophobe | | | |
|---|---|---|---|---|---|---|---|---|
| Mirs | Mean 1 | Mean 2 | fold | pVal | Mean 1 | Mean 2 | fold | pVal |
| hsa-miR-221 | 12.94 | 16.59 | 12.59 | 1.50E−43 | 15.89 | 16.59 | 1.63 | 4.60E−05 |
| hsa-miR-222 | 13.32 | 16.81 | 11.29 | 1.70E−40 | 15.8 | 16.81 | 2.02 | 7.80E−10 |
| hsa-miR-210 | 12.19 | 9.33 | 7.25 | 1.40E−22 | 9.59 | 9.33 | 1.2 | 2.50E−01 |
| hsa-miR-21 | 16.61 | 13.83 | 6.9 | 2.50E−32 | 13.57 | 13.83 | 1.2 | 2.50E−01 |
| hsa-miR-455-3p | 10.69 | 7.71 | 7.87 | 1.00E−27 | 8.54 | 7.71 | 1.77 | 2.90E−04 |
| hsa-miR-122 | 5.64 | 5.7 | NaN | NaN | 5.64 | 5.7 | NaN | NaN |
| hsa-miR-126 | 11.06 | 13.01 | 3.86 | 1.10E−19 | 13.63 | 13.01 | 1.54 | 6.00E−04 |
| hsa-miR-31 | 13.59 | 9.46 | 17.46 | 2.10E−17 | 8.06 | 9.46 | 2.64 | 3.20E−03 |
| hsa-miR-195 | 10.49 | 10.63 | 1.1 | 4.80E−01 | 11.3 | 10.63 | 1.59 | 3.40E−04 |
| hsa-miR-182 | 9.16 | 10.69 | 2.9 | 4.30E−08 | 10.1 | 10.69 | 1.51 | 3.50E−02 |
| MID-19962 | 11.55 | 11.55 | 1 | 1.00E+00 | 13.19 | 11.55 | 3.13 | 5.70E−08 |
| hsa-miR-139-5p | 6.75 | 8.51 | 3.37 | 1.40E−16 | 10.44 | 8.51 | 3.82 | 7.60E−15 |
| hsa-miR-200c | 8 | 13.49 | 45.22 | 1.20E−28 | 8.34 | 13.49 | 35.57 | 1.80E−17 |
| hsa-miR-141 | 6.62 | 11.82 | 36.81 | 4.70E−34 | 7.25 | 11.82 | 23.77 | 9.10E−19 |
| hsa-miR-200b | 13.48 | 13.14 | 1.27 | 4.20E−02 | 10.76 | 13.14 | 5.22 | 4.90E−12 |
| hsa-miR-551b | 9.15 | 6.6 | 5.86 | 5.60E−13 | 9.24 | 6.6 | 6.26 | 1.80E−10 |
| hsa-miR-200a | 12.71 | 12.03 | 1.59 | 6.40E−06 | 10.25 | 12.03 | 3.45 | 7.40E−09 |
| MID-16582 | 15.05 | 15.17 | 1.08 | 6.10E−01 | 17.05 | 15.17 | 3.68 | 4.50E−12 |
| hsa-miR-130a | 11.71 | 10.17 | 2.92 | 1.30E−17 | 11.31 | 10.17 | 2.21 | 7.70E−11 |
| hsa-miR-93 | 12.57 | 11.47 | 2.14 | 1.00E−13 | 11.07 | 11.47 | 1.32 | 3.40E−03 |
| MID-16869 | 10.14 | 11.18 | 2.05 | 1.00E−03 | 9.42 | 11.18 | 3.38 | 1.40E−06 |
| hsa-miR-146a | 10.51 | 8.35 | 4.48 | 1.40E−20 | 8.25 | 8.35 | 1.07 | 5.40E−01 |
| MID-00536 | 13.13 | 14.03 | 1.87 | 3.40E−05 | 14.94 | 14.03 | 1.87 | 8.20E−08 |
| hsa-miR-192 | 9.88 | 8.35 | 2.9 | 2.40E−05 | 7.91 | 8.35 | 1.35 | 1.60E−01 |

Example 2

Specific microRNAs are Able to Distinguish Between Different Subtypes of Renal Tumor Samples as Measured by qRT-PCR The analysis of qRT-PCR results of 134 tumor samples obtained from patients diagnosed with oncocytoma, clear cell RCC, papillary RCC and chromophobe RCC exhibited a significant difference in the expression pattern of multiple miRs, as demonstrated in FIGS. 7-12. These miRs are presented in Table 4.

TABLE 4 miR expression as measured by RT-PCR distinguishing between different subtypes of renal tumor samples, numbers of expression in this table are 50-Ct

| Mirs | Mean 1 | Mean 2 | fold | pVal | Mean 1 | Mean 2 | fold | pVal |
|---|---|---|---|---|---|---|---|---|
| | Clear Vs Papillary | | | | Clear Vs Oncocytoma | | | |
| hsa-miR-221 | 21.48 | 22.95 | 2.77 | 3.10E−07 | 21.48 | 25.92 | 21.64 | 4.70E−29 |
| hsa-miR-222 | 20.96 | 21.73 | 1.71 | 8.80E−04 | 20.96 | 23.8 | 7.18 | 1.50E−21 |
| hsa-miR-210 | 22.37 | 21.63 | 1.67 | 1.30E−02 | 22.37 | 18.22 | 17.72 | 7.30E−23 |
| hsa-miR-21 | 26.58 | 27.88 | 2.47 | 2.10E−07 | 26.58 | 24.4 | 4.52 | 2.10E−12 |
| hsa-miR-455-3p | 19.51 | 19.75 | 1.18 | 1.80E−01 | 19.51 | 17.03 | 5.58 | 6.40E−16 |
| hsa-miR-122 | 18.79 | 11.61 | 145.29 | 5.90E−22 | 18.79 | 12.16 | 99.18 | 1.60E−23 |
| hsa-miR-126 | 24.84 | 22.71 | 4.4 | 7.60E−19 | 24.84 | 24.49 | 1.28 | 1.20E−02 |

TABLE 4-continued miR expression as measured by RT-PCR distinguishing between different subtypes of renal tumor samples, numbers of expression in this table are 50-Ct

| Mirs | Mean 1 | Mean 2 | fold | pVal | Mean 1 | Mean 2 | fold | pVal |
|---|---|---|---|---|---|---|---|---|
| hsa-miR-31 | 20.45 | 24.82 | 20.66 | 5.50E−17 | 20.45 | 19.59 | 1.82 | 8.90E−03 |
| hsa-miR-195 | 22.79 | 21.32 | 2.78 | 3.50E−11 | 22.79 | 21.52 | 2.41 | 1.80E−11 |
| hsa-miR-182 | 14.44 | 17.82 | 10.4 | 1.30E−14 | 14.44 | 18.49 | 16.5 | 6.10E−22 |
| MID-19962 | 22.69 | 25.23 | 5.8 | 1.50E−09 | 22.69 | 26.88 | 18.28 | 6.10E−22 |
| hsa-miR-139-5p | 20.42 | 20.03 | 1.31 | 8.60E−02 | 20.42 | 21.89 | 2.78 | 3.30E−08 |
| hsa-miR-200c | 18.41 | 19.95 | 2.91 | 1.10E−04 | 18.41 | 19.09 | 1.59 | 1.70E−01 |
| hsa-miR-141 | 17.74 | 19.36 | 3.09 | 3.10E−10 | 17.74 | 17.3 | 1.35 | 2.60E−01 |
| hsa-miR-200b | 19 | 21.45 | 5.47 | 1.90E−17 | 19 | 18.55 | 1.37 | 1.70E−01 |
| | Clear Vs Chromophobe | | | | Papillary Vs Oncocytoma | | | |
| hsa-miR-221 | 21.48 | 26.46 | 31.42 | 1.70E−32 | 22.95 | 25.92 | 7.81 | 4.40E−21 |
| hsa-miR-222 | 20.96 | 25.11 | 17.8 | 1.60E−30 | 21.73 | 23.8 | 4.21 | 1.40E−17 |
| hsa-miR-210 | 22.37 | 18.58 | 13.81 | 1.30E−18 | 21.63 | 18.22 | 10.64 | 2.50E−17 |
| hsa-miR-21 | 26.58 | 24.47 | 4.32 | 4.90E−14 | 27.88 | 24.4 | 11.17 | 1.20E−19 |
| hsa-miR-455-3p | 19.51 | 16.51 | 8.04 | 1.70E−17 | 19.75 | 17.03 | 6.57 | 3.50E−18 |
| hsa-miR-122 | 18.79 | 14.67 | 17.42 | 1.80E−15 | 11.61 | 12.16 | 1.46 | 2.90E−01 |
| hsa-miR-126 | 24.84 | 24.18 | 1.59 | 8.40E−05 | 22.71 | 24.49 | 3.45 | 9.90E−16 |
| hsa-miR-31 | 20.45 | 21.56 | 2.16 | 4.30E−03 | 24.82 | 19.59 | 37.67 | 8.10E−23 |
| hsa-miR-195 | 22.79 | 21.38 | 2.65 | 2.50E−12 | 21.32 | 21.52 | 1.15 | 2.60E−01 |
| hsa-miR-182 | 14.44 | 19.62 | 36.03 | 5.00E−25 | 17.82 | 18.49 | 1.59 | 1.60E−02 |
| MID-19962 | 22.69 | 25.15 | 5.51 | 1.40E−08 | 25.23 | 26.88 | 3.15 | 8.80E−06 |
| hsa-miR-139-5p | 20.42 | 20.9 | 1.4 | 3.50E−02 | 20.03 | 21.89 | 3.63 | 1.60E−09 |
| hsa-miR-200c | 18.41 | 24.01 | 48.29 | 3.50E−25 | 19.95 | 19.09 | 1.83 | 8.20E−02 |
| hsa-miR-141 | 17.74 | 22.37 | 24.82 | 3.50E−25 | 19.36 | 17.3 | 4.18 | 1.40E−06 |
| hsa-miR-200b | 19 | 21.19 | 4.57 | 1.90E−20 | 21.45 | 18.55 | 7.47 | 4.90E−12 |
| | Papillary Vs Chromophobe | | | | Oncocytoma Vs Chromophobe | | | |
| hsa-miR-221 | 22.95 | 26.46 | 11.34 | 8.70E−26 | 25.92 | 26.46 | 1.45 | 2.40E−03 |
| hsa-miR-222 | 21.73 | 25.11 | 10.43 | 8.20E−29 | 23.8 | 25.11 | 2.48 | 2.20E−12 |
| hsa-miR-210 | 21.63 | 18.58 | 8.29 | 1.50E−13 | 18.22 | 18.58 | 1.28 | 2.60E−01 |
| hsa-miR-21 | 27.88 | 24.47 | 10.67 | 1.20E−21 | 24.4 | 24.47 | 1.05 | 8.00E−01 |
| hsa-miR-455-3p | 19.75 | 16.51 | 9.46 | 2.60E−19 | 17.03 | 16.51 | 1.44 | 7.70E−02 |
| hsa-miR-122 | 11.61 | 14.67 | 8.34 | 4.90E−08 | 12.16 | 14.67 | 5.69 | 2.00E−07 |
| hsa-miR-126 | 22.71 | 24.18 | 2.78 | 8.30E−11 | 24.49 | 24.18 | 1.24 | 5.10E−02 |
| hsa-miR-31 | 24.82 | 21.56 | 9.58 | 2.30E−11 | 19.59 | 21.56 | 3.93 | 1.80E−07 |
| hsa-miR-195 | 21.32 | 21.38 | 1.05 | 7.30E−01 | 21.52 | 21.38 | 1.1 | 3.80E−01 |
| hsa-miR-182 | 17.82 | 19.62 | 3.46 | 1.10E−07 | 18.49 | 19.62 | 2.18 | 1.10E−05 |
| MID-19962 | 25.23 | 25.15 | 1.05 | 8.60E−01 | 26.88 | 25.15 | 3.32 | 1.10E−05 |
| hsa-miR-139-5p | 20.03 | 20.9 | 1.83 | 1.10E−03 | 21.89 | 20.9 | 1.99 | 3.80E−04 |
| hsa-miR-200c | 19.95 | 24.01 | 16.59 | 7.80E−19 | 19.09 | 24.01 | 30.29 | 4.40E−16 |
| hsa-miR-141 | 19.36 | 22.37 | 8.04 | 3.90E−16 | 17.3 | 22.37 | 33.6 | 2.30E−18 |
| hsa-miR-200b | 21.45 | 21.19 | 1.2 | 1.60E−01 | 18.55 | 21.19 | 6.24 | 4.80E−12 |

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method for distinguishing between oncocytoma, clear cell renal cell carcinoma (RCC), papillary (chromaphil) RCC and chromophobe RCC in a human subject with renal cancer, the method comprising:
   (a) obtaining a kidney tumor sample from the human subject;
   (b) determining an expression profile in said sample of SEQ ID NOS: 1-24 by contacting the sample with probes that hybridize to each of SEQ ID NOS: 1-24, wherein each probe comprises the complement of one of SEQ ID NOs: 1-24, and wherein the probes are attached to a solid substrate;
   (c) comparing said expression profile to a reference threshold value by using a classifier algorithm; and
   (d) determining whether the human subject has oncocytoma, clear cell renal cell carcinoma (RCC), papillary (chromaphil) RCC or chromophobe RCC based on altered expression of SEQ ID NOS: 1-24 in the sample relative to the reference threshold value; wherein increased expression of SEQ ID NOS: 3, 5, 7, 9, 11, 12, 16, 18, 19 and 23 relative to the reference threshold is indicative of the presence of oncocytoma; wherein increased expression of SEQ ID NOS: 1, 2, 4, 6, 8, 10, 13-15, 17, 20-22 and 24 is indicative of the presence of chromophobe RCC; wherein increased expression of SEQ ID NOS: 3, 5-7, 9, 12 and 24 is indicative of the presence of clear cell RCC; and wherein increased expression of SEQ ID NOS: 1, 2, 4, 8, 10, 11 and 13-23 is indicative of the presence of papillary RCC.

2. The method of claim 1, wherein the classifier algorithm is selected from the group consisting of decision tree classifier, K-nearest neighbor classifier (KNN), logistic regression classifier, nearest neighbor classifier, neural network classifier, Gaussian mixture model (GMM), Support Vector Machine (SVM) classifier, nearest centroid classifier, linear regression classifier and random forest classifier.

3. The method of claim 1, wherein said kidney tumor sample is a fresh, frozen, fixed, wax-embedded or formalin fixed paraffin-embedded (FFPE) kidney tumor sample.

4. The method of claim 1, further comprising isolating RNA from the sample, and labeling the isolated RNA.

5. The method of claim 1, wherein the solid substrate comprises a solid-phase nucleic acid biochip array.

6. The method of claim 5, wherein the probes are attached to the array with a linker of 10-60 nucleotides.

7. A method for distinguishing between chromophobe RCC and oncocytoma in a human subject with renal cancer, the method comprising:
   (a) obtaining a kidney tumor sample from the human subject;
   (b) determining in said sample an expression profile of SEQ ID NOS: 1-24 by contacting the sample with probes that hybridize to each of SEQ ID NOS: 1-24, wherein each probe comprises the complement of one of SEQ ID NOs: 1-24, and wherein the probes are attached to a solid substrate;
   (c) comparing said expression profile to a reference threshold value; and
   (d) determining whether the human subject has oncocytoma or chromophobe RCC based on altered expression of SEQ ID NOS: 1-24 relative to the reference threshold value; wherein increased expression of SEQ ID NOS: 1, 2, 4, 6, 8, 10, 13-15, 17, 20-22 and 24 is indicative of the presence of chromophobe RCC; and wherein increased expression of SEQ ID NOS: 3, 5, 7, 9, 11, 12, 16, 18, 19 and 23 relative to the reference threshold is indicative of the presence of oncocytoma.

8. A method for distinguishing between clear cell RCC and papillary RCC in a human subject with renal cancer, the method comprising:
   (a) obtaining a kidney tumor sample from the human subject;
   (b) determining in said sample an expression profile of SEQ ID NOS: 1-24 by contacting the sample with probes that hybridize to each of SEQ ID NOS: 1-24, wherein each probe comprises the complement of one of SEQ ID NOs: 1-24, and wherein the probes are attached to a solid substrate;
   (c) comparing said expression profile to a reference threshold value; and
   (d) determining whether the human subject has clear cell RCC or papillary RCC based on altered expression of SEQ ID NOS: 1-24 relative to the reference threshold value; wherein increased expression of SEQ ID NOS: 3, 5-7, 9, 12 and 24 is indicative of the presence of clear cell RCC; and wherein increased expression of SEQ ID NOS: 1, 2, 4, 8, 10, 11 and 13-23 is indicative of the presence of papillary RCC.

* * * * *

SEQUENCE LISTING

<160> NUMBER OF SEQ ID NOS: 82

<210> SEQ ID NO 1
<211> LENGTH: 23
<212> TYPE: RNA
<213> ORGANISM: Homo sapiens

<400> SEQUENCE: 1
agcuacauug ucugcugggu uuc                23

<210> SEQ ID NO 2
<211> LENGTH: 21
<212> TYPE: RNA
<213> ORGANISM: Homo sapiens

<400> SEQUENCE: 2
agcuacaucu ggcuacuggg u                                              21

<210> SEQ ID NO 3
<211> LENGTH: 22
<212> TYPE: RNA
<213> ORGANISM: Homo sapiens

<400> SEQUENCE: 3
cugugcgugu gacagcggcu ga                                             22

<210> SEQ ID NO 4
<211> LENGTH: 22
<212> TYPE: RNA
<213> ORGANISM: Homo sapiens

<400> SEQUENCE: 4
uagcuuauca gacugauguu ga                                             22

<210> SEQ ID NO 5
<211> LENGTH: 21
<212> TYPE: RNA
<213> ORGANISM: Homo sapiens

<400> SEQUENCE: 5
gcaguccaug ggcauauaca c                                              21

<210> SEQ ID NO 6
<211> LENGTH: 22
<212> TYPE: RNA
<213> ORGANISM: Homo sapiens

<400> SEQUENCE: 6
uggaguguga caauggucuu ug                                             22

<210> SEQ ID NO 7
<211> LENGTH: 22
<212> TYPE: RNA
<213> ORGANISM: Homo sapiens

<400> SEQUENCE: 7
ucguaccgug aguaauaaug cg                                             22

<210> SEQ ID NO 8
<211> LENGTH: 21
<212> TYPE: RNA
<213> ORGANISM: Homo sapiens

<400> SEQUENCE: 8
aggcaagaug cuggcauagc u                                              21

<210> SEQ ID NO 9
<211> LENGTH: 21
<212> TYPE: RNA
<213> ORGANISM: Homo sapiens

<400> SEQUENCE: 9
uagcagcaca gaaauauugg c                                              21

```
<210> SEQ ID NO 10
<211> LENGTH: 24
<212> TYPE: RNA
<213> ORGANISM: Homo sapiens

<400> SEQUENCE: 10
uuuggcaaug guagaacuca cacu                                              24

<210> SEQ ID NO 11
<211> LENGTH: 19
<212> TYPE: RNA
<213> ORGANISM: Homo sapiens

<400> SEQUENCE: 11
uaaaaggaac ucggcaaau                                                    19

<210> SEQ ID NO 12
<211> LENGTH: 22
<212> TYPE: RNA
<213> ORGANISM: Homo sapiens

<400> SEQUENCE: 12
ucuacagugc acgugucucc ag                                                22

<210> SEQ ID NO 13
<211> LENGTH: 23
<212> TYPE: RNA
<213> ORGANISM: Homo sapiens

<400> SEQUENCE: 13
uaauacugcc ggguaaugau gga                                               23

<210> SEQ ID NO 14
<211> LENGTH: 22
<212> TYPE: RNA
<213> ORGANISM: Homo sapiens

<400> SEQUENCE: 14
uaacacuguc ugguaaagau gg                                                22

<210> SEQ ID NO 15
<211> LENGTH: 22
<212> TYPE: RNA
<213> ORGANISM: Homo sapiens

<400> SEQUENCE: 15
uaauacugcc ugguaaugau ga                                                22

<210> SEQ ID NO 16
<211> LENGTH: 21
<212> TYPE: RNA
<213> ORGANISM: Homo sapiens

<400> SEQUENCE: 16
gcgacccaua cuugguuuca g                                                 21

<210> SEQ ID NO 17
<211> LENGTH: 22
<212> TYPE: RNA
<213> ORGANISM: Homo sapiens

<400> SEQUENCE: 17
```
uaacacuguc ugguaacgau gu        22

<210> SEQ ID NO 18
<211> LENGTH: 19
<212> TYPE: RNA
<213> ORGANISM: Homo sapiens

<400> SEQUENCE: 18
agugaagcau uggacugua        19

<210> SEQ ID NO 19
<211> LENGTH: 22
<212> TYPE: RNA
<213> ORGANISM: Homo sapiens

<400> SEQUENCE: 19
cagugcaaug uuaaaagggc au        22

<210> SEQ ID NO 20
<211> LENGTH: 23
<212> TYPE: RNA
<213> ORGANISM: Homo sapiens

<400> SEQUENCE: 20
caaagugcug uucgugcagg uag        23

<210> SEQ ID NO 21
<211> LENGTH: 22
<212> TYPE: RNA
<213> ORGANISM: Homo sapiens

<400> SEQUENCE: 21
augugggugg uggucaccgu uu        22

<210> SEQ ID NO 22
<211> LENGTH: 22
<212> TYPE: RNA
<213> ORGANISM: Homo sapiens

<400> SEQUENCE: 22
ugagaacuga auuccauggg uu        22

<210> SEQ ID NO 23
<211> LENGTH: 21
<212> TYPE: RNA
<213> ORGANISM: Homo sapiens

<400> SEQUENCE: 23
uagggugcuu agcuguuaac u        21

<210> SEQ ID NO 24
<211> LENGTH: 21
<212> TYPE: RNA
<213> ORGANISM: Homo sapiens

<400> SEQUENCE: 24
cugaccuaug aauugacagc c        21

<210> SEQ ID NO 25
<211> LENGTH: 110
<212> TYPE: RNA
<213> ORGANISM: Homo sapiens

<400> SEQUENCE: 25

```
ugaacaucca ggucuggggc augaaccugg cauacaaugu agauuucugu guucguuagg    60
caacagcuac auugucugcu ggguuucagg cuaccuggaa acauguucuc              110
```

<210> SEQ ID NO 26
<211> LENGTH: 110
<212> TYPE: RNA
<213> ORGANISM: Homo sapiens

<400> SEQUENCE: 26

```
gcugcuggaa gguguaggua cccucaaugg cucaguagcc aguguagauc cugucuuucg    60
uaaucagcag cuacaucugg cuacggguc ucgauggca cuucuagcu                  110
```

<210> SEQ ID NO 27
<211> LENGTH: 110
<212> TYPE: RNA
<213> ORGANISM: Homo sapiens

<400> SEQUENCE: 27

```
acccggcagu gccuccaggc cagggcagc cccugcccac cgcacacugc gcugcccag     60 acccacugug cgugugacag cggcugaucu gugccugggc agcgcgaccc              110
```

<210> SEQ ID NO 28
<211> LENGTH: 72
<212> TYPE: RNA
<213> ORGANISM: Homo sapiens

<400> SEQUENCE: 28

```
ugucggguag cuuaucagac ugauguugac uguugaaucu cauggcaaca ccagucgaug    60
ggcugucuga ca                                                        72
```

<210> SEQ ID NO 29
<211> LENGTH: 96
<212> TYPE: RNA
<213> ORGANISM: Homo sapiens

<400> SEQUENCE: 29

```
ucccuggcgu gagggaugu gccuuuggac uacaucgugg aagccagcac caugcaguccc    60 augggcauau acacuugccu caaggccuau gucauc                              96
```

<210> SEQ ID NO 30
<211> LENGTH: 85
<212> TYPE: RNA
<213> ORGANISM: Homo sapiens

<400> SEQUENCE: 30

```
ccuuagcaga gcugggagu gugacaaugg uguuugguc uaaacuauca aacgccauua    60
ucacacuaaa uagcuacugc uaggc                                          85
```

<210> SEQ ID NO 31
<211> LENGTH: 85
<212> TYPE: RNA
<213> ORGANISM: Homo sapiens

<400> SEQUENCE: 31

```
cgcuggcgac gggacauuau acuuuuggu acgcgcugug acacuucaaa cucguaccgu    60
gaguaauaau gcgccgucca cggca                                         85
```

<210> SEQ ID NO 32

```
<211> LENGTH: 71
<212> TYPE: RNA
<213> ORGANISM: Homo sapiens

<400> SEQUENCE: 32
ggagaggagg caagaugcug gcauagcugu ugaacuggga accugcuaug ccaacauauu    60
gccaucuuuc c                                                        71

<210> SEQ ID NO 33
<211> LENGTH: 87
<212> TYPE: RNA
<213> ORGANISM: Homo sapiens

<400> SEQUENCE: 33
agcuucccug gcucuagcag cacagaaaua uuggcacagg gaagcgaguc ugccaauauu    60
ggcugugcug cuccaggcag gguggug                                       87

<210> SEQ ID NO 34
<211> LENGTH: 110
<212> TYPE: RNA
<213> ORGANISM: Homo sapiens

<400> SEQUENCE: 34
gagcugcuug ccuccccccg uuuuuggcaa ugguagaacu cacacuggug agguaacagg    60
auccgguggu ucuagacuug ccaacuaugg ggcgaggacu cagccggcac              110

<210> SEQ ID NO 35
<211> LENGTH: 66
<212> TYPE: RNA
<213> ORGANISM: Homo sapiens

<400> SEQUENCE: 35
acaggcaugc ucuaaggaaa gguuaaaaaa aauuaaaagg aacucggcaa auuuuacccu    60
gccugu                                                              66

<210> SEQ ID NO 36
<211> LENGTH: 89
<212> TYPE: RNA
<213> ORGANISM: Homo sapiens

<400> SEQUENCE: 36
uguuaaucca acacaggcau gcucuaagga aauauuacaa aaaguaaaag gaacucggca    60
aaucuuaccc caccuguuua ccaaaaaca                                     89

<210> SEQ ID NO 37
<211> LENGTH: 68
<212> TYPE: RNA
<213> ORGANISM: Homo sapiens

<400> SEQUENCE: 37
guguauucua cagugcacgu gucccagug uggcucggag gcuggagacg cggcccuguu    60
ggaguaac                                                            68

<210> SEQ ID NO 38
<211> LENGTH: 68
<212> TYPE: RNA
<213> ORGANISM: Homo sapiens

<400> SEQUENCE: 38
cccucgucuu acccagcagu guuugggugc gguugggagu cucuaauacu gccggguaau    60
```

```
                                                     gauggagg                                                                68

<210> SEQ ID NO 39
<211> LENGTH: 95
<212> TYPE: RNA
<213> ORGANISM: Homo sapiens

<400> SEQUENCE: 39
cggccggccc uggguccauc uuccaguaca guguuggaug gucuaauugu gaagcuccua        60
acacugucug guaaagaugg cucccgggug gguuc                                   95

<210> SEQ ID NO 40
<211> LENGTH: 95
<212> TYPE: RNA
<213> ORGANISM: Homo sapiens

<400> SEQUENCE: 40
ccagcucggg cagccguggc caucuuacug ggcagcauug gauggaguca ggucucuaau        60
acugccuggu aaugaugacg gcggagcccu gcacg                                   95

<210> SEQ ID NO 41
<211> LENGTH: 96
<212> TYPE: RNA
<213> ORGANISM: Homo sapiens

<400> SEQUENCE: 41
agaugugcuc uccuggccca ugaaaucaag cgugggugag accuggugca gaacgggaag        60
gcgacccaua cuugguuuca gaggcuguga gaauaa                                  96

<210> SEQ ID NO 42
<211> LENGTH: 90
<212> TYPE: RNA
<213> ORGANISM: Homo sapiens

<400> SEQUENCE: 42 ccgggcccu gugagcaucu uaccggacag ugcuggauuu cccagcuuga cucuaacacu         60
gucugguaac gauguucaaa ggugacccgc                                         90

<210> SEQ ID NO 43
<211> LENGTH: 89
<212> TYPE: RNA
<213> ORGANISM: Homo sapiens

<400> SEQUENCE: 43
ugcugcuggc cagagcucuu uucacauugu gcuacugucu gcaccuguca cuagcagugc        60
aauguuaaaa gggcauuggc cguguagug                                          89

<210> SEQ ID NO 44
<211> LENGTH: 80
<212> TYPE: RNA
<213> ORGANISM: Homo sapiens

<400> SEQUENCE: 44 cuggggcuc caaagugcug uucgugcagg uagugugauu acccaaccua cugcugagcu        60
agcacuuccc gagccccgg                                                     80

<210> SEQ ID NO 45
<211> LENGTH: 76
<212> TYPE: RNA
```

```
<213> ORGANISM: Homo sapiens

<400> SEQUENCE: 45
agagaauagu caacggucgg cgaacaucag uggggguang guaaaauggc ugagugaagc    60
auuggacugu aaaucu                                                   76

<210> SEQ ID NO 46
<211> LENGTH: 71
<212> TYPE: RNA
<213> ORGANISM: Homo sapiens

<400> SEQUENCE: 46
gagugaagca uuggacugua aaucuaaaga cagggcuaa gccucuuuuu accagcucug    60
aggugauuuu c                                                        71

<210> SEQ ID NO 47
<211> LENGTH: 130
<212> TYPE: RNA
<213> ORGANISM: Homo sapiens

<400> SEQUENCE: 47
uggcaugucu ggcuugggaa augauggga uaaugugggu ggguggucacc guuuagacaa    60 agucuacaua aauuucaauu acuaccugca gcauccccu gcacauaccu cguccggag    120 cuagagucca                                                         130

<210> SEQ ID NO 48
<211> LENGTH: 99
<212> TYPE: RNA
<213> ORGANISM: Homo sapiens

<400> SEQUENCE: 48
ccgaugugua uccucagcuu ugagaacuga auccauggg uugugucagu gucagaccuc    60
ugaaauucag uucuucagcu gggauaucuc ugucaucgu                          99

<210> SEQ ID NO 49
<211> LENGTH: 115
<212> TYPE: RNA
<213> ORGANISM: Homo sapiens

<400> SEQUENCE: 49
gaaguagauu gaagccaguu gauuaggguag cuuagcuguu aacuaagugu uugugggguuu   60 aagucccauu ggucuaguaa gggcuuagcu uaauuaaagu ggcugauuug cguuc         115

<210> SEQ ID NO 50
<211> LENGTH: 108
<212> TYPE: RNA
<213> ORGANISM: Homo sapiens

<400> SEQUENCE: 50
guagauugaa gccaguugau uaggggucuu agcuguuaac uaaguguuug uggguuuaag    60
ucccauuggu cuaguaaggg cuuagcuuaa uuaaagugg cugauuugc                108

<210> SEQ ID NO 51
<211> LENGTH: 110
<212> TYPE: RNA
<213> ORGANISM: Homo sapiens

<400> SEQUENCE: 51
gccgagaccg agugcacagg gcucugaccu augaauugac agccagugcu cucgucuccc    60
```

```
cucuggcugc aauuccaua ggucacaggu auguucgccu caaugccagc              110
```

<210> SEQ ID NO 52
<211> LENGTH: 28
<212> TYPE: DNA
<213> ORGANISM: artificial sequence
<220> FEATURE:
<223> OTHER INFORMATION: Synthetic

<400> SEQUENCE: 52

```
cagtcatttg ggagctacat ctggctac                                     28
```

<210> SEQ ID NO 53
<211> LENGTH: 28
<212> TYPE: DNA
<213> ORGANISM: artificial sequence
<220> FEATURE:
<223> OTHER INFORMATION: Synthetic

<400> SEQUENCE: 53

```
cagtcatttg ggtaatactg cctggtaa                                     28
```

<210> SEQ ID NO 54
<211> LENGTH: 28
<212> TYPE: DNA
<213> ORGANISM: artificial sequence
<220> FEATURE:
<223> OTHER INFORMATION: Synthetic

<400> SEQUENCE: 54

```
cagtcatttg gctagcttat cagactga                                     28
```

<210> SEQ ID NO 55
<211> LENGTH: 28
<212> TYPE: DNA
<213> ORGANISM: artificial sequence
<220> FEATURE:
<223> OTHER INFORMATION: Synthetic

<400> SEQUENCE: 55

```
cagtcatttg gctgtgcgt gtgacagc                                      28
```

<210> SEQ ID NO 56
<211> LENGTH: 28
<212> TYPE: DNA
<213> ORGANISM: artificial sequence
<220> FEATURE:
<223> OTHER INFORMATION: Synthetic

<400> SEQUENCE: 56

```
cagtcatttg ggagctacat tgtctgct                                     28
```

<210> SEQ ID NO 57
<211> LENGTH: 28
<212> TYPE: DNA
<213> ORGANISM: artificial sequence
<220> FEATURE:
<223> OTHER INFORMATION: Synthetic

<400> SEQUENCE: 57

```
cagtcatttg ggtttggcaa tggtagaa                                     28
```

<210> SEQ ID NO 58
<211> LENGTH: 21
<212> TYPE: DNA

```
<213> ORGANISM: artificial sequence
<220> FEATURE:
<223> OTHER INFORMATION: Synthetic

<400> SEQUENCE: 58
ggctctacag tgcacgtgtc t                                              21

<210> SEQ ID NO 59
<211> LENGTH: 28
<212> TYPE: DNA
<213> ORGANISM: artificial sequence
<220> FEATURE:
<223> OTHER INFORMATION: Synthetic

<400> SEQUENCE: 59
cagtcatttg ggtcgtaccg tgagtaat                                       28

<210> SEQ ID NO 60
<211> LENGTH: 28
<212> TYPE: DNA
<213> ORGANISM: artificial sequence
<220> FEATURE:
<223> OTHER INFORMATION: Synthetic

<400> SEQUENCE: 60
cagtcatttg gctagcagca cagaaata                                       28

<210> SEQ ID NO 61
<211> LENGTH: 28
<212> TYPE: DNA
<213> ORGANISM: artificial sequence
<220> FEATURE:
<223> OTHER INFORMATION: Synthetic

<400> SEQUENCE: 61
cagtcatttg gcgcagtcca tgggcata                                       28

<210> SEQ ID NO 62
<211> LENGTH: 28
<212> TYPE: DNA
<213> ORGANISM: artificial sequence
<220> FEATURE:
<223> OTHER INFORMATION: Synthetic

<400> SEQUENCE: 62
cagtcatttg ggtggagtgt gacaatgg                                       28

<210> SEQ ID NO 63
<211> LENGTH: 21
<212> TYPE: DNA
<213> ORGANISM: artificial sequence
<220> FEATURE:
<223> OTHER INFORMATION: Synthetic

<400> SEQUENCE: 63
aggcaagatg ctggcatagc t                                              21

<210> SEQ ID NO 64
<211> LENGTH: 28
<212> TYPE: DNA
<213> ORGANISM: artificial sequence
<220> FEATURE:
<223> OTHER INFORMATION: Synthetic

<400> SEQUENCE: 64
cagtcatttg gctaaaagga actcggca                                       28
```

<210> SEQ ID NO 65
<211> LENGTH: 28
<212> TYPE: DNA
<213> ORGANISM: artificial sequence
<220> FEATURE:
<223> OTHER INFORMATION: Synthetic

<400> SEQUENCE: 65
cagtcatttg ggtaatactg ccgggtaa                              28

<210> SEQ ID NO 66
<211> LENGTH: 28
<212> TYPE: DNA
<213> ORGANISM: artificial sequence
<220> FEATURE:
<223> OTHER INFORMATION: Synthetic

<400> SEQUENCE: 66
cagtcatttg ggtaacactg tctggtaa                              28

<210> SEQ ID NO 67
<211> LENGTH: 25
<212> TYPE: DNA
<213> ORGANISM: artificial sequence
<220> FEATURE:
<223> OTHER INFORMATION: Synthetic

<400> SEQUENCE: 67
atccgttttt tttttttacc cagta                                 25

<210> SEQ ID NO 68
<211> LENGTH: 23
<212> TYPE: DNA
<213> ORGANISM: artificial sequence
<220> FEATURE:
<223> OTHER INFORMATION: Synthetic

<400> SEQUENCE: 68 ccgtttttt tttttcatca tta                                    23

<210> SEQ ID NO 69
<211> LENGTH: 23
<212> TYPE: DNA
<213> ORGANISM: artificial sequence
<220> FEATURE:
<223> OTHER INFORMATION: Synthetic

<400> SEQUENCE: 69 ccgtttttt tttttcaaca tca                                    23

<210> SEQ ID NO 70
<211> LENGTH: 22
<212> TYPE: DNA
<213> ORGANISM: artificial sequence
<220> FEATURE:
<223> OTHER INFORMATION: Synthetic

<400> SEQUENCE: 70
cgtttttttt ttttcagccg ct                                    22

<210> SEQ ID NO 71
<211> LENGTH: 22
<212> TYPE: DNA
<213> ORGANISM: artificial sequence
<220> FEATURE:

<223> OTHER INFORMATION: Synthetic

<400> SEQUENCE: 71 cgttttttttt ttttgaaacc ca                                    22

<210> SEQ ID NO 72
<211> LENGTH: 24
<212> TYPE: DNA
<213> ORGANISM: artificial sequence
<220> FEATURE:
<223> OTHER INFORMATION: Synthetic

<400> SEQUENCE: 72 tccgttttttt tttttagtg tgag                                   24

<210> SEQ ID NO 73
<211> LENGTH: 18
<212> TYPE: DNA
<213> ORGANISM: artificial sequence
<220> FEATURE:
<223> OTHER INFORMATION: Synthetic

<400> SEQUENCE: 73
aaaaccgata gtgagtcg                                          18

<210> SEQ ID NO 74
<211> LENGTH: 23
<212> TYPE: DNA
<213> ORGANISM: artificial sequence
<220> FEATURE:
<223> OTHER INFORMATION: Synthetic

<400> SEQUENCE: 74
ccgttttttt tttttcgcat tat                                    23

<210> SEQ ID NO 75
<211> LENGTH: 23
<212> TYPE: DNA
<213> ORGANISM: artificial sequence
<220> FEATURE:
<223> OTHER INFORMATION: Synthetic

<400> SEQUENCE: 75
ccgttttttt tttttgccaa tat                                    23

<210> SEQ ID NO 76
<211> LENGTH: 23
<212> TYPE: DNA
<213> ORGANISM: artificial sequence
<220> FEATURE:
<223> OTHER INFORMATION: Synthetic

<400> SEQUENCE: 76
ccgttttttt tttttgtgta tat                                    23

<210> SEQ ID NO 77
<211> LENGTH: 22
<212> TYPE: DNA
<213> ORGANISM: artificial sequence
<220> FEATURE:
<223> OTHER INFORMATION: Synthetic

<400> SEQUENCE: 77 cgttttttttt ttttcaaaca cc                                    22

```
-continued

<210> SEQ ID NO 78
<211> LENGTH: 18
<212> TYPE: DNA
<213> ORGANISM: artificial sequence
<220> FEATURE:
<223> OTHER INFORMATION: Synthetic

<400> SEQUENCE: 78
aaaaccgata gtgagtcg                                                 18

<210> SEQ ID NO 79
<211> LENGTH: 23
<212> TYPE: DNA
<213> ORGANISM: artificial sequence
<220> FEATURE:
<223> OTHER INFORMATION: Synthetic

<400> SEQUENCE: 79 ccgtttttt tttttatttg ccg                                            23

<210> SEQ ID NO 80
<211> LENGTH: 22
<212> TYPE: DNA
<213> ORGANISM: artificial sequence
<220> FEATURE:
<223> OTHER INFORMATION: Synthetic

<400> SEQUENCE: 80 cgttttttt tttccatca tt                                              22

<210> SEQ ID NO 81
<211> LENGTH: 22
<212> TYPE: DNA
<213> ORGANISM: artificial sequence
<220> FEATURE:
<223> OTHER INFORMATION: Synthetic

<400> SEQUENCE: 81 cgttttttt tttccatct tt                                              22

<210> SEQ ID NO 82
<211> LENGTH: 22
<212> TYPE: DNA
<213> ORGANISM: artificial sequence
<220> FEATURE:
<223> OTHER INFORMATION: Synthetic

<400> SEQUENCE: 82
gcgagcacag aattaatacg ac                                            22
```